(12) United States Patent
Liljestrand et al.

(10) Patent No.: US 6,200,531 B1
(45) Date of Patent: Mar. 13, 2001

(54) APPARATUS FOR CARRYING OUT ELECTROCHEMILUMINESCENCE TEST MEASUREMENTS

(75) Inventors: John Liljestrand, Ijamsville, MD (US); Jue Zhang, Vienna; David R. Gambrel, Oakton, both of VA (US); Sergey Ivanov, Germantown; Jacob N. Wohlstadter, Rockville, both of MD (US)

(73) Assignee: IGEN International, Inc., Gaithersburg, MD (US)

( * ) Notice: Subject to any disclaimer, the term of this patent is extended or adjusted under 35 U.S.C. 154(b) by 0 days.

(21) Appl. No.: 09/076,325

(22) Filed: May 11, 1998

(51) Int. Cl.[7] .................................................. G01N 21/64
(52) U.S. Cl. ......................................... 422/52; 250/361 C
(58) Field of Search ................................ 422/52, 82.07, 422/82.08; 250/361 C, 458.1, 461.1; 436/172

(56) References Cited

U.S. PATENT DOCUMENTS

| | | |
|---|---|---|
| 3,676,784 | 7/1972 | Le Comte et al. . |
| 3,816,795 | 6/1974 | Maricle et al. . |
| 3,961,253 | 6/1976 | Brych . |

(List continued on next page.)

FOREIGN PATENT DOCUMENTS

| | | |
|---|---|---|
| 1247962 | 11/1986 | (JP) . |
| WO86/02734 | 5/1986 | (WO) . |
| WO87/07386 | 12/1987 | (WO) . |
| WO92/14139 | 8/1992 | (WO) . |
| WO98/12539 | 3/1998 | (WO) . |

OTHER PUBLICATIONS

Arora, A. et al., 1997, "Sub–Microliter Electrochemiluminescence Detector—A Model for Small Volume Analysis Systems", *Analytical Communications*, 34: 393–395.

Greenway, G.M., 1990, "Analytical Applications of Electrogenerated Chemiluminescence", *Trends in Analytical Chemistry*, 9: 200–203.

Greenway. G.M. et al., 1995, "Determination of Oxyprenolol by Electrogenerated Chemiluminescence", *Analytical Proceedings Including Analytical Communications*, 32: 251–253.

Hsueh, Y.T. et al., 1996, "A Microfabricated, Electrochemiluminescence Cell for the Detection of Amplified DNA", *Sensors and Actuators B*, 33: 110–114.

Knight, A.W. et al., 1995, "Development of a Silicon Photodiode, Electrogenerated Chemiluminescence, Flow–Through Detector", *Analytical Proceedings Including Analytical Communications*, 32: 125–127.

Ikariyama, I., et al., Apr. 30, 1985, "Electrochemical Luminescence–based Homogeneous Immunoassay", *Biochemical and Biophysical Research Comm.*, vol. 128, No. 2, pp. 987–992.

*Primary Examiner*—Jeffrey Snay
(74) *Attorney, Agent, or Firm*—Kramer Levin Naftalis & Frankel LLP

(57) ABSTRACT

Apparatus for the conduct of electrochemiluminescence measurements includes an ECL chamber having a transparent window defining one wall of the chamber and a photodetector mounted closely adjacent thereto. An assay fluid is subject to a magnetic field and is electrically energized. Electrochemiluminescence induced in the fluid is measured by the photodetector.

6 Claims, 14 Drawing Sheets

U.S. PATENT DOCUMENTS

| | | |
|---|---|---|
| 3,984,688 | 10/1976 | Von Bargen et al. . |
| 4,007,011 | 2/1977 | Greaves et al. . |
| 4,210,724 | 7/1980 | Sogi et al. . |
| 4,213,703 | 7/1980 | Haunold et al. . |
| 4,280,815 | 7/1981 | Oberhardt et al. . |
| 4,297,105 | 10/1981 | Dube . |
| 4,303,410 | 12/1981 | Copeland . |
| 4,431,919 | 2/1984 | Kostlin et al. . |
| 4,443,713 | 4/1984 | Layton . |
| 4,537,861 | 8/1985 | Elings et al. . |
| 4,771,215 | 9/1988 | Munakata et al. . |
| 4,849,340 | 7/1989 | Oberhardt . |
| 5,061,445 | 10/1991 | Zoski et al. . |
| 5,068,088 | 11/1991 | Hall et al. . |
| 5,093,268 | 3/1992 | Leventis et al. . |
| 5,112,646 | 5/1992 | Koshi et al. . |
| 5,132,227 | 7/1992 | Kelly . |
| 5,147,806 | 9/1992 | Kamin et al. . |
| 5,240,863 | 8/1993 | Shibue et al. . |
| 5,247,243 | 9/1993 | Hall et al. . |
| 5,296,191 | 3/1994 | Hall et al. . |
| 5,298,427 | 3/1994 | Bobbitt et al. . |
| 5,310,687 | 5/1994 | Bard et al. . |
| 5,324,457 | 6/1994 | Zhang et al. . |
| 5,451,528 | 9/1995 | Raymoure et al. . |
| 5,466,416 | 11/1995 | Ghaed et al. . |
| 5,538,687 * | 7/1996 | Kotzan et al. .......................... 422/52 |
| 5,541,113 * | 7/1996 | Siddigi et al. .......................... 436/56 |
| 5,589,136 * | 12/1996 | Northrup et al. .................... 422/102 |
| 5,624,637 * | 4/1997 | Ghaed et al. .......................... 422/52 |
| 5,705,402 | 1/1998 | Leland et al. . |
| 5,716,842 | 2/1998 | Baier . |
| 5,720,922 | 2/1998 | Ghaed et al. . |
| 5,744,367 | 4/1998 | Talley et al. . |
| 5,746,974 * | 5/1998 | Massey et al. ......................... 422/52 |
| 5,779,976 | 7/1998 | Leland et al. . |
| 5,786,141 * | 7/1998 | Bard et al. ............................... 435/6 |

* cited by examiner

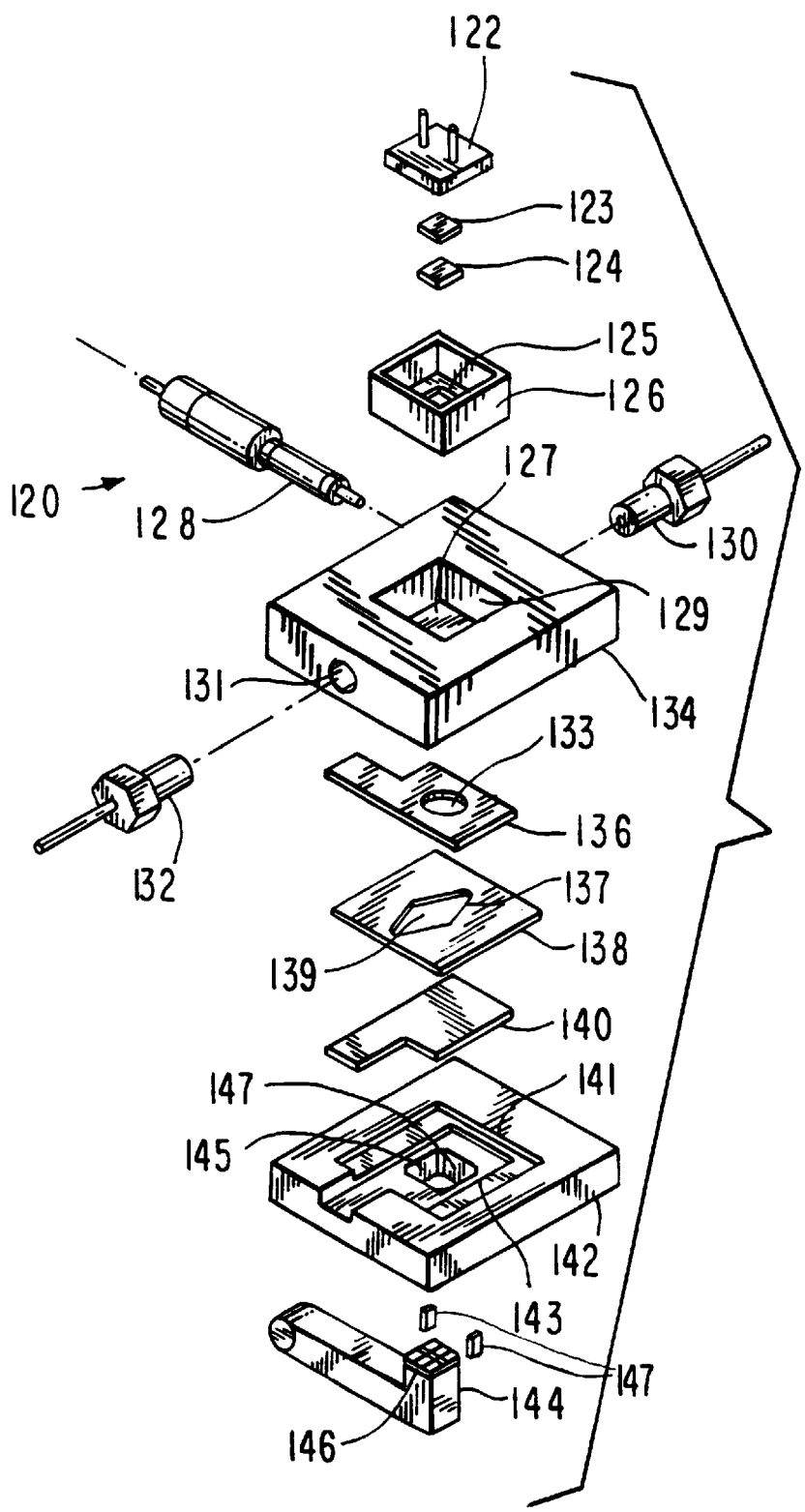

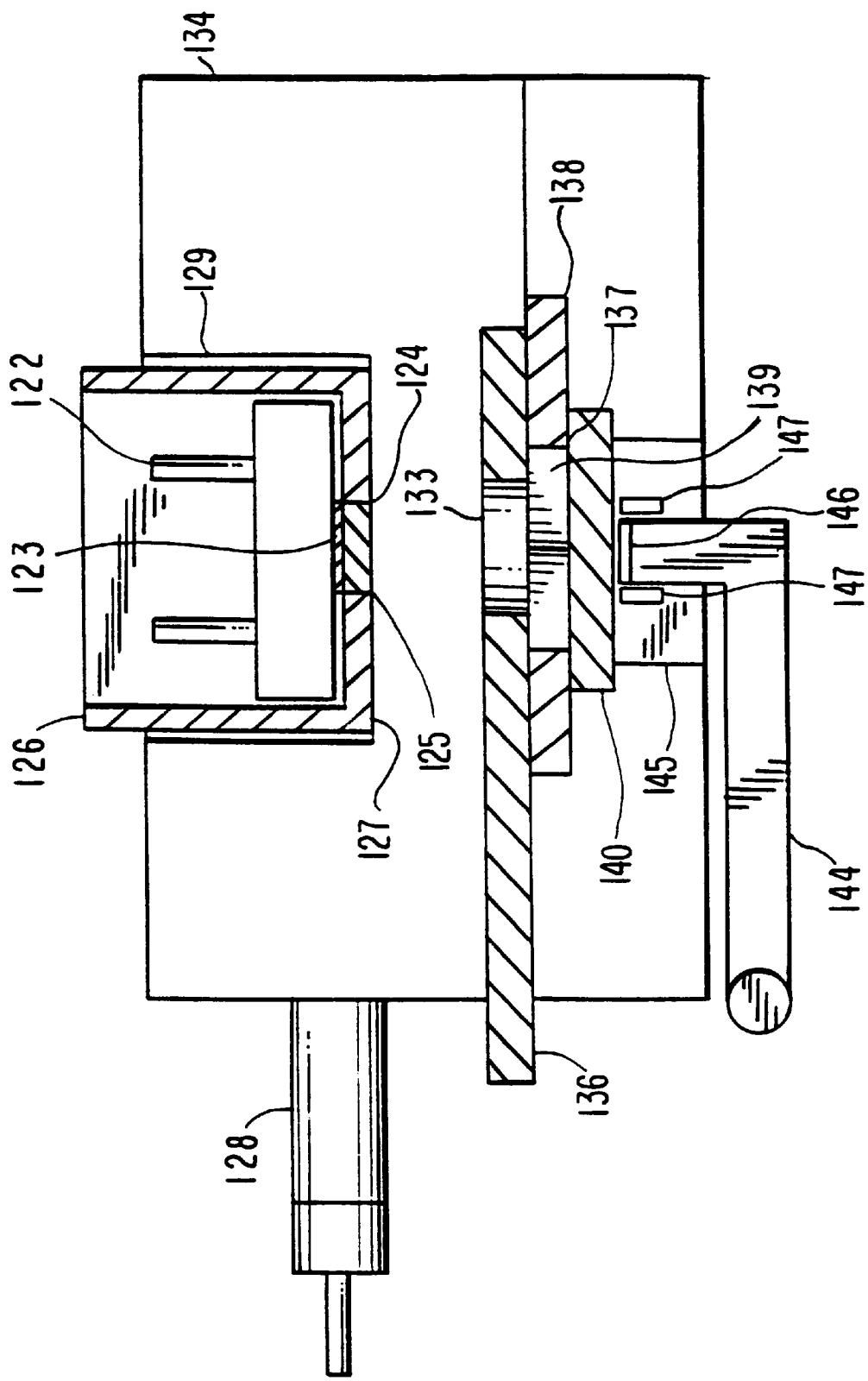

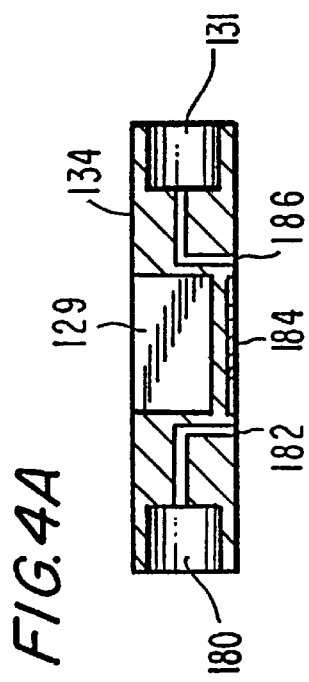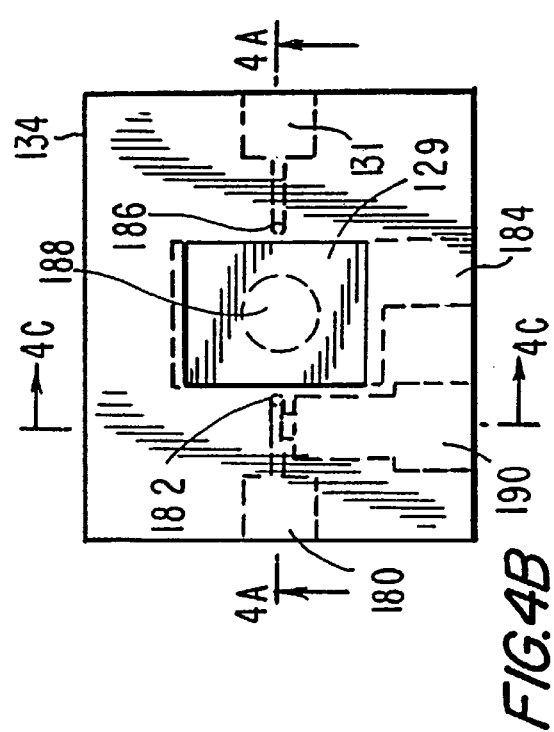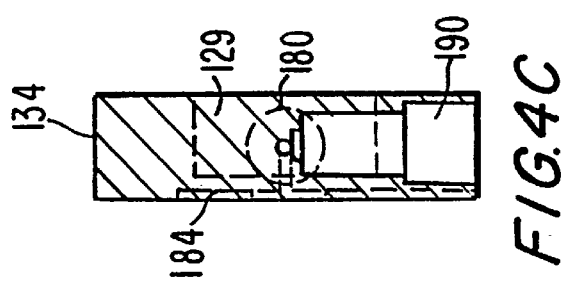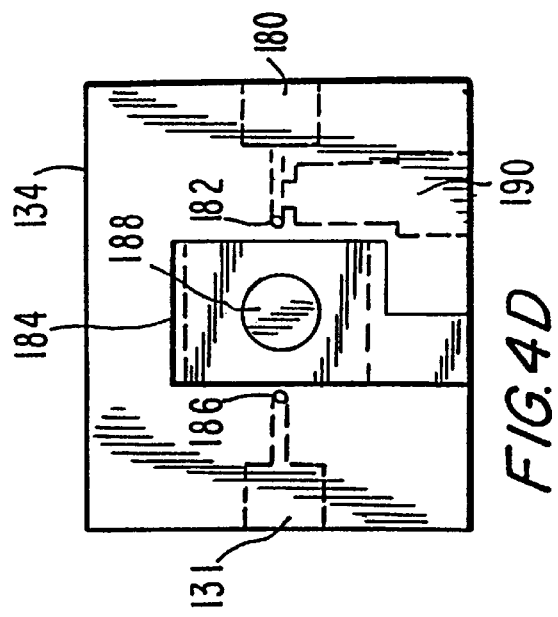

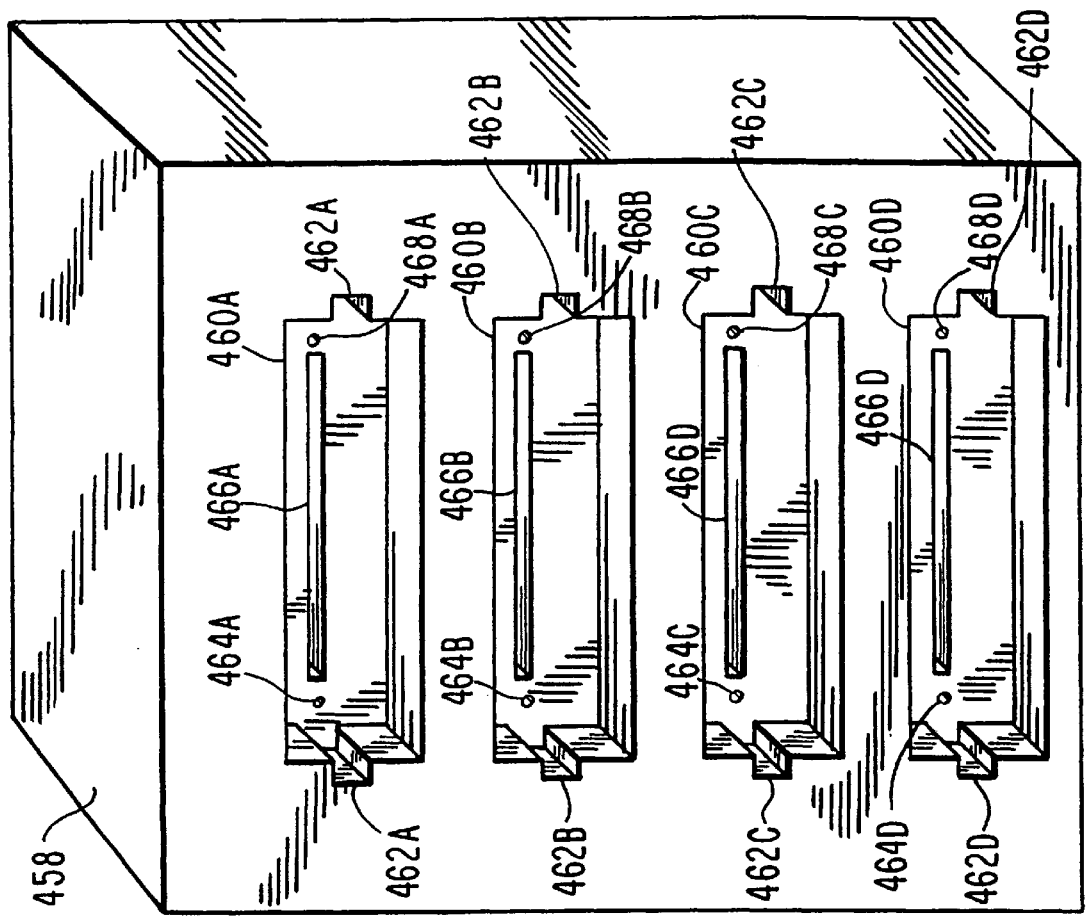
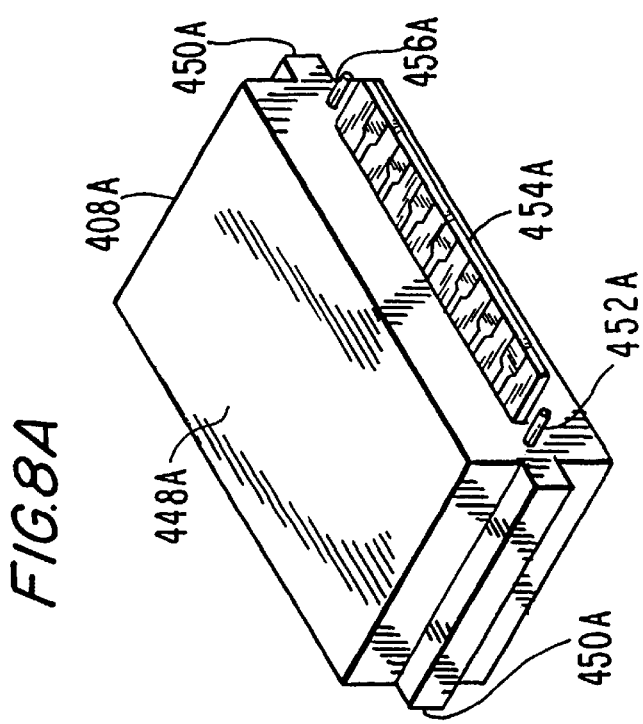
FIG.8A
FIG.8B

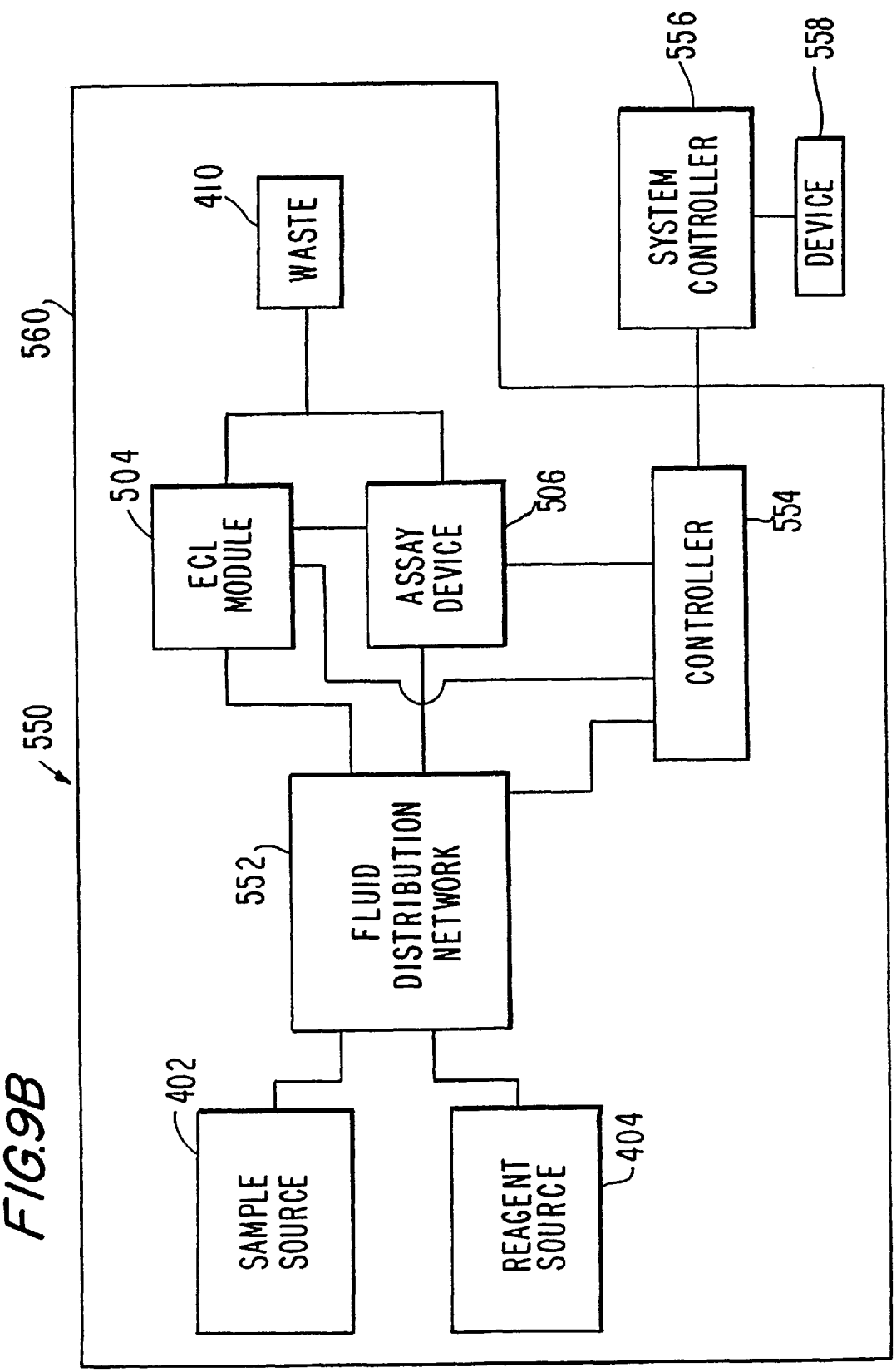

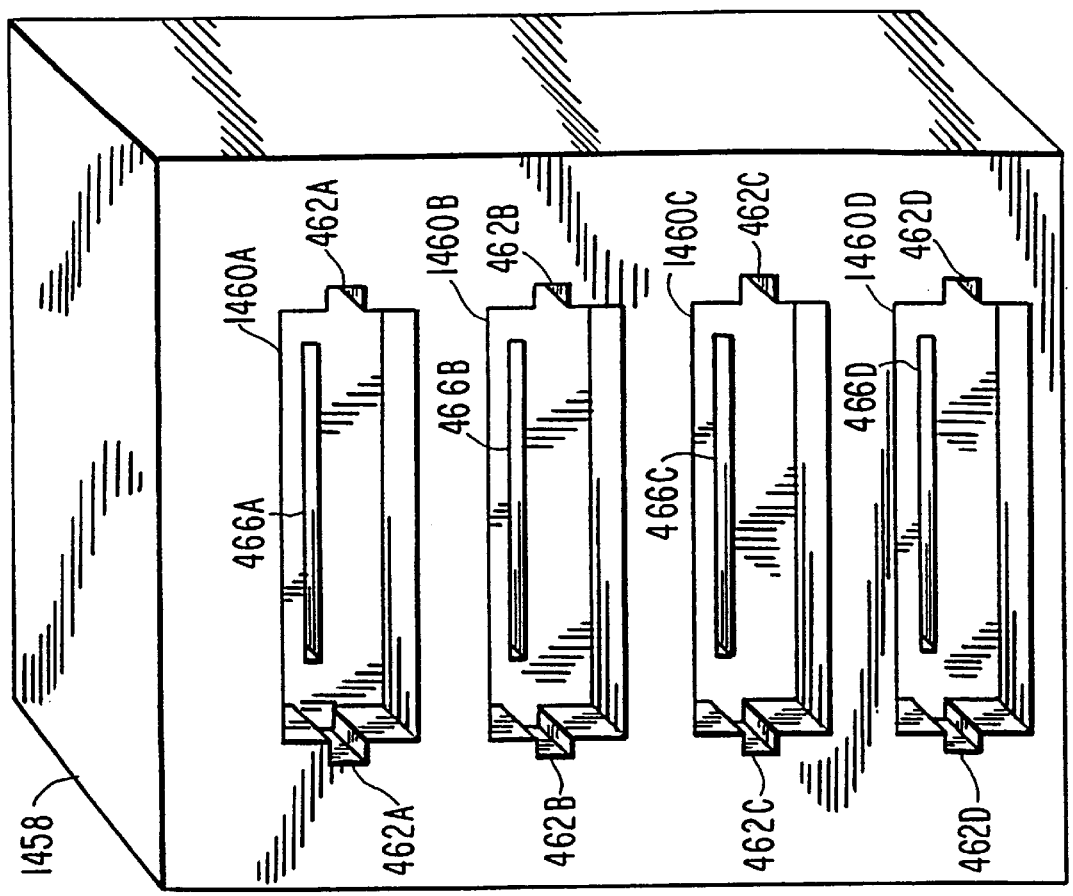
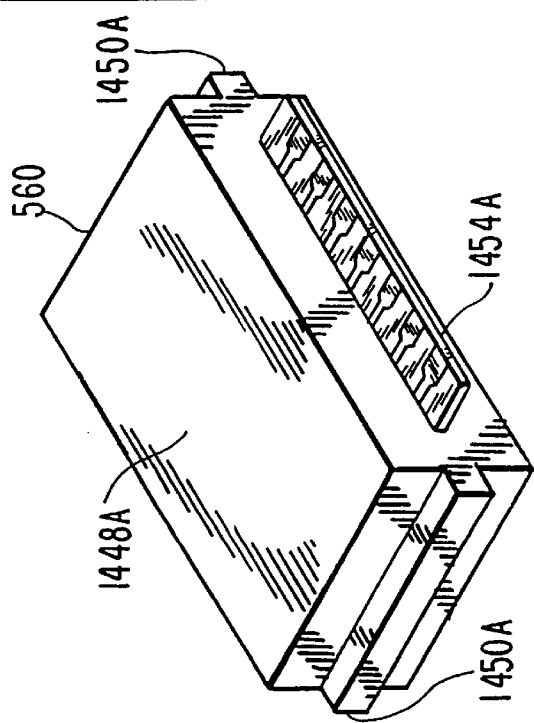

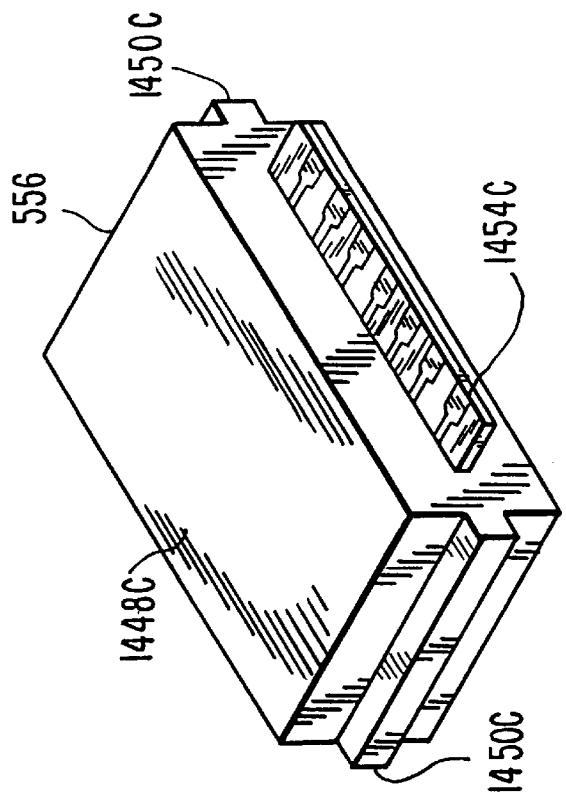
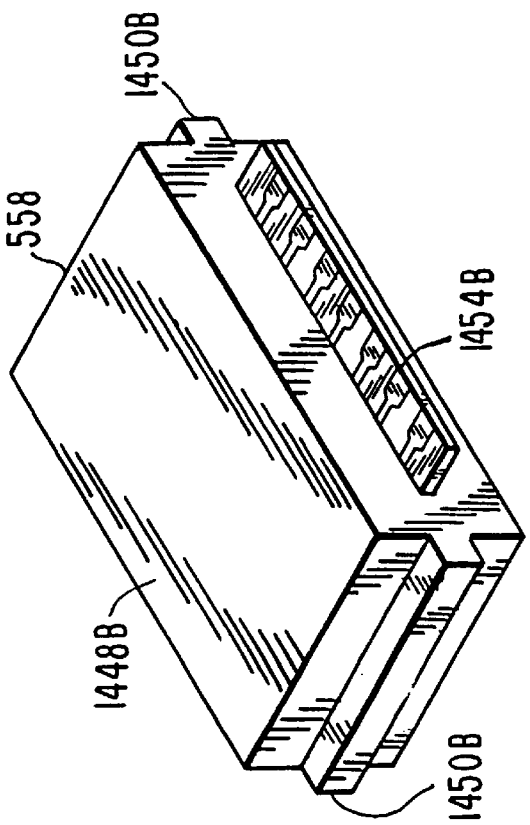

APPARATUS FOR CARRYING OUT ELECTROCHEMILUMINESCENCE TEST MEASUREMENTS

BACKGROUND OF THE INVENTION

Field of the Invention

This application relates generally to apparatus and methods for detecting and measuring analytes of interest by inducing electrochemiluminescence (ECL) in a test sample and detecting the resulting light.

Numerous methods and systems have been developed for detecting and quantitating analytes of interest in chemical, biochemical, biological, and environmental samples. Methods and systems that are capable of measuring toxins, environmental contaminants, pharmacological agents, bioactive substances, metabolites, pathogenic organisms, proteins and nucleic acids are of substantial value to researchers and clinicians. At this time, there are a number of commercially available instruments that utilize ECL for analytical measurements. These instruments have demonstrated exceptional performance.

The high cost, complex engineering and long development time required to custom-design and manufacture ECL instruments have delayed broad implementation of ECL technology. Clearly, there remains a need for ECL subsystems or modules that can be easily adapted to a broad variety of different applications.

Current needs for precision analytical testing instrumentation are extraordinarily diverse. For example, pharmaceutical screening analyses require instruments that can perform large numbers of analyses at very high speeds on very small quantities of sample. In addition, such instruments may need to perform many different types of highly sensitive quantitative tests utilizing different detection methods. Similarly, clinical diagnostic analyses for human health care typically require highly sensitive and exceptionally reliable instrumentation. In contrast, it is expected that commercial instruments intended for field use would be small, perhaps portable, simple to use, and operable with only limited power. Low production and maintenance costs are often predominant considerations.

Description of the Prior Art

An apparatus for carrying out electrochemiluminescence test measurements is found in U.S. Pat. No. 5,466,416 assigned to IGEN, Inc. A cross-sectional view of a flow cell is depicted in FIG. 1. Flow cell 18 comprises a removable plug 20, a gasket 22, a retainer block 24, a counter electrode 26, an ECL test chamber 28, a working electrode 30, a transparent block 32, a counter electrode 34, a retainer block 36, a conduit 46, a main housing 48, a chamber 40, a lateral block 42, a frit 44, a gasket 50, a plug 52, an O-ring seal 56, a threaded coupling 58, a conduit 60, a pivot arm 61, a magnet 62, and a threaded coupling 64.

Flow cell 18 includes a main housing 48 formed of a durable, transparent and chemically inert material such as acrylic or polymethyl methacrylate. Threaded coupling 64 defines a fluid inlet in a lower surface of housing 48 and is contiguous with conduit 46. Conduit 46 extends through housing 48 from coupling 64 to an upper surface of housing 48. Threaded coupling 58 defines a fluid outlet in a lower surface of housing 48 and is contiguous with conduit 60. Conduit 60 extends through housing 48 from coupling 58 to the upper surface of housing 48. ECL test chamber 28 is bounded by the upper surface of housing 48, a lower surface of block 32, lower and side surfaces of counter electrodes 26 and 34, the upper surface of working electrode 30, and the interior surface of gasket 22. Chamber 28 communicates with both conduit 60 and conduit 46. Fluid introduced through coupling 64 may travel through conduit 46 to chamber 28 and exit through conduit 60 and coupling 58.

Working electrode 30, counter electrode 26, and counter electrode 34 may consist of electrically-conductive materials such as platinum or gold. Working electrode 30 has a generally flat, elongate, rectangular shape having a longitudinal axis arranged generally transverse to a longitudinal axis of chamber 28. Electrode 30 is positioned centrally between conduits 60 and 46 in a shallow groove formed in the upper surface of housing 48. An adhesive (not shown) bonds electrode 30 to the groove in housing 48. Accordingly, at least three seams between electrode 30 and housing 48 abut chamber 28; one on each latitudinal side of electrode 30 and a third at a longitudinal end of electrode 30. As displayed in FIG. 1, electrode 30 is approximately as wide as the gap between counter electrodes 26 and 34 and is positioned centrally therebetween.

Counter electrodes 26 and 34 have an "L"-shaped cross-section, the shorter arm having a length slightly longer than the thickness of block 32 and the longer arm having a length of less than half of the width of block 32. The two arms of each electrode are flat, thin and positioned perpendicular to each other but in different planes. The widths of electrodes 26 and 34 are approximately less than half of the thickness of block 32. Counter electrode 26 is affixed to a side of transparent block 32 and is held in place by retainer block 24. On the opposite side of transparent block 32, counter electrode 34 is similarly affixed by retainer block 36.

Magnet 62 is affixed to pivot arm 61. In its raised position, pivot arm 61 positions magnet 62 beneath working electrode 30, sandwiching a segment of housing 48 therebetween. In its lowered position, pivot arm 61 pivots down and away from housing 48 thereby significantly increasing the distance between working electrode 30 and magnet 62.

A reference electrode assembly, integrated into housing 48, comprises chamber 40, block 42, gasket 50, frit 44, plug 52, and gasket 56. An ionic fluid (not shown) is retained within chamber 40. Chamber 40 comprises a cavity defined by housing 48, gasket 50 and block 42. Frit 44 extends into conduit 60 and is sealed by O-ring 56 and plug 52 to prevent fluidic interchange.

A refill aperture (not shown) is provided in housing 48 to allow replacement of the ionic fluid held in chamber 40. The refill aperture is sealed by removable plug 20. To achieve useful and reproducible ECL test measurements, flow cell 18 utilized a temperature-controlled environment. FIG. 2 illustrates an apparatus 80 from U.S. Pat. No. 5,466,416 for providing a temperature-controlled environment for flow cell 18. Apparatus 80 comprises a photomultiplier tube (PMT) 82, an insulating cover 92, a housing 94, a plurality of foil heaters 96, a circuit board 84, flow cell 18, a magnet 62, a pivot arm 61, a linear actuator 98, a coil spring 102, an air space 90, and a fan 104. For reference purposes, housing 48, block 42, retainer block 24, counter electrode 26, and block 32 are specifically labelled on flow cell 18.

Foil heaters 96 are positioned on the outer lateral surfaces and the outer lower surface of housing 94. The upper surface of housing 94 adjacent PMT 82 is formed of a transparent material while the remaining portions of housing 94 are preferable opaque. Insulating cover 92 covers foil heaters 96 as well as the remaining uncovered outer surfaces of housing 94 to provide thermal insulation and prevent the entry of light into flow cell 18. PMT 82 is a conventional photomultiplier tube mounted on the upper surface of housing 94. PMT 82 is physically large compared to the size of the flow cell, requires a high-voltage power supply, and is highly sensitive to the surrounding temperature and the presence of magnetic fields. It is preferable that PMT 82 be maintained at a relatively low temperature. Flow cell 18 is positioned below PMT 82 inside temperature-controlled housing 94.

Circuit board 84, incorporating operating electronics for apparatus 80, is mounted on an interior surface of housing 94 adjacent flow cell 18. As shown, linear actuator 98 is connected to coil spring 102 which, in turn, is connected to pivot arm 61. Magnet 62 is affixed to an end of pivot arm 61.

The temperature within housing 94 is controlled through the operation of foil heaters 96 in conjunction with fan 104. Fan 104, affixed to the interior surface of housing 94, circulates air within air space 90. Air space 90 extends throughout the interior of housing 94 and surrounds each component therein, including, specifically, flow cell 18. Air space 90 further includes an air gap between the upper surface of flow cell 18, e.g., block 32, and the upper interior surface of housing 94.

As described above, pivot arm 61, shown in its lowered position, can pivot upward to place magnet 62 within housing 48 of flow cell 18. Linear actuator 98, operating in conjunction with coil spring 102, causes pivot arm 61 to move.

In an ordinary operation, magnet 62 is raised into a position adjacent to working electrode 30 of flow cell 18 to attract magnetic particles in an assay fluid in chamber 28 to the vicinity of working electrode 30. Shortly thereafter, to avoid magnetic interference with the operation of PMT 82, magnet 62 is withdrawn from flow cell 18 prior to the induction of electrochemiluminescence in the assay sample fluid. Conventionally, magnet 62 is not positioned to collect magnetic particles during the application of electrical energy to the assay fluid. Magnet 62 is usually retracted before electrochemiluminescence is induced to avoid magnetic interference with ECL measurements by PMT 82. Removal of the magnetic field from working electrode 30 may allow a flowing assay sample fluid to carry away magnetic particles collected there.

Methods of calibration for apparatus 80 convolve diagnosis of the effectiveness of bead capture and the effectiveness of the ECL cell. Therefore, calibration is preferably achieved using bead-based standards (e.g. magnetic beads coated with ECL labels).

As shown, apparatus 80 includes thermal insulation between PMT 82 and flow cell 18. PMT 82 is very temperature-sensitive in that heat increases the background noise signal generated by PMT 82. Typically, PMT 82 is maintained in a moderate to low temperature environment. Since the ECL process generates considerable heat, flow cell 18 is thermally isolated from PMT 82. The use of thermal insulating material between flow cell 18 and PMT 82 increases the length of the optical path from working electrode 30 to PMT 82 and, therefore, reduces the efficiency with which light emitted at working electrode 30 is transmitted to PMT 82.

Additionally, it should be readily apparent that the optical path between chamber 28 of flow cell 18 and PMT 82 includes multiple air-solid and solid-solid boundaries. These transitions between media reduce the amount of ECL-generated light which ultimately reaches PMT 82. Light generated between counter electrode 26 and working electrode 30 or between counter electrode 34 and working electrode 30 passes from the assay fluid in chamber 28 through a bottom surface of block 32, through the bulk of block 32 and through the upper surface of block 32. At the lower surface of block 32, light is reflected back towards housing 48 and, in particular, working electrode 30. Light travelling through the bulk of block 32 is diffused and may be gradually separated into component wavelengths. At the upper surface of block 32, a portion of the incident light is internally reflected back into the bulk of block 32 while the remainder is transmitted into air space 90. Additionally, at the boundary between block 32 and air space 90, the light rays will be bent away from PMT 82 due to the decrease in refractive index across the boundary. Consequently, the amount of light directed towards PMT 82 is reduced.

The light travels through air space 90 to the lower surface of housing 94 where, again, some light is reflected back towards flow cell 18 while the remainder is transmitted into the bulk of housing 94. Within the bulk of housing 94, the light is diffused and may be further caused to separate into component wavelengths. At the upper surface of housing 94, where PMT 82 abuts housing 94, a portion of the light is internally reflected into the bulk of housing 94 while a remainder portion is transmitted to PMT 82. The aforedescribed diffusion, bending, and reflection of light may significantly reduce the amount of ECL-generated light which is actually incident upon PMT 82.

As shown, flow cell 18 includes electrode-housing seams within ECL chamber 28. The adhesive present at these seams and used to affix working electrode 30 to housing 48 may deteriorate and erode over time. As a result, assay fluid components, cleaning fluid components, or other materials may collect in the seams between electrode 30 and housing 48. The collected materials may react with or otherwise contaminate components of subsequent assays and thereby affect assay results.

OBJECTS OF THE INVENTION

It is, therefore, a primary object of the present invention to provide apparatus and methodology for carrying out improved electrochemiluminescence test measurements.

A further object of the invention is to provide apparatus and methodology for the efficient detection of light generated during an electrochemiluminescence assay.

Still a further and related object of the invention is to provide a modular ECL measurement apparatus for rapid and efficient incorporation into an application-specific diagnostic device.

Another object of the invention is to provide apparatus and methodology for conducting electrochemiluminescence test measurements under conditions of continuous fluid flow upon an assay sample containing magnetic particles.

A still further object of the invention is to provide apparatus and methodology for applying a magnetic field to assay materials during the induction of electrochemiluminescence and simultaneously detecting the light generated thereby.

Another object of the invention is to provide apparatus that integrates each of the components needed to perform an ECL measurement in a single open-architecture ECL module.

Yet another object of the invention is to provide a modular apparatus for carrying out an ECL measurement that comprises a modular system interface.

A further object of the invention is to provide apparatus and methodology for an integrated system for assaying one or more samples for one or more analytes of interest.

A related object of the invention is to provide apparatus for conducting multiple simultaneous or near-simultaneous ECL measurements and for sharing an assay sample sampling device, a power supply, a controller, a system interface, and a user interface.

An additional object of the invention is to provide apparatus and methodology for normalizing the operations of two or more ECL modules.

Another object of the invention is to provide an apparatus for ECL measurements that comprises a modular system interface that is adapted for convenient coupling to other analytical or processing devices.

Another object of the invention is to provide apparatus and systems capable of detecting analytes in a sample by means of electrochemiluminescence and one or more other analytical techniques.

Still another object of the invention is to provide an integrated system for processing samples, amplifying nucleic acids, and measuring nucleic acids.

SUMMARY OF THE INVENTION

These and other objects of the invention are achieved in an apparatus for the conduct of electrochemiluminescence measurements which includes a cell having at least one cell wall which includes a transparent portion adjacent to an ECL chamber defined within the cell, a working electrode abutting the ECL chamber and in optical registration with the transparent portion, a counter electrode abutting the ECL chamber and an electrically-shielded window adjacent to and in optical registration with the transparent portion of the cell wall.

The apparatus of the invention may also include a photodetector, e.g. a photodiode, in optical registration with the electrically-shielded window, the transparent portion of the cell wall and the working electrode.

In preferred embodiments of the invention, the working electrode is removably fitted within the cell and has a planar electrode surface abutting the ECL chamber such that no seam is created between the working electrode and the ECL chamber. A removable magnet is provided for applying a magnetic field to the working electrode.

The object of creating an integrated system for assaying a sample or plurality of samples for a plurality of analytes of interest is also achieved in systems comprising a plurality of modules which may share a common sample handling subsystem, a common power supply, a common controller and/or a common system or user interface.

According to an aspect of the present invention an apparatus for the conduct of electrochemiluminescence measurements includes a cell having at least one cell wall which includes a transparent portion adjacent to an ECL chamber defined within the cell, a working electrode abutting the ECL chamber and in optical registration with the transparent portion, a counter electrode abutting the ECL chamber, and an electrically-shielded window adjacent to and in optical registration with the transparent portion.

According to another aspect of the present invention an apparatus for the conduct of electrochemiluminescence measurements includes a cell having at least one cell wall which includes a transparent portion adjacent to an ECL chamber defined within the cell, a working electrode abutting the ECL chamber and in optical registration with the transparent portion, a counter electrode abutting the ECL chamber, a photodiode in optical registration with the transparent portion, and an optical filter adjacent to and in optical registration with the transparent portion.

According to another aspect of the present invention an apparatus for the conduct of electrochemiluminescence measurements includes a cell having at least one cell wall which includes a transparent portion adjacent to an ECL chamber defined within the cell, a working electrode abutting the ECL chamber and in optical registration with the transparent portion, and a counter electrode abutting the ECL chamber and having an aperture in optical registration with the transparent portion.

According to still another aspect of the present invention an apparatus for the conduct of electrochemiluminescence measurements includes a cell having at least one cell wall which includes a transparent portion adjacent to an ECL chamber defined within the cell, a working electrode abutting the ECL chamber and in optical registration with the transparent portion, and a counter electrode abutting the ECL chamber, wherein the working electrode is removably fitted within the cell and has a planar electrode surface abutting the ECL chamber.

According to still another aspect of the present invention an apparatus for the conduct of electrochemiluminescence measurements includes a cell having at least one cell wall which includes a transparent portion adjacent to an ECL chamber defined within the cell, a working electrode having a planar electrode surface abutting the ECL chamber and in optical registration with the transparent portion of the cell wall, the working electrode being positioned within the cell such that no seam between the working electrode and the cell abuts the ECL chamber, and a counter electrode abutting the ECL chamber.

According to still another aspect of the present invention an apparatus for the conduct of electrochemiluminescence measurements includes a cell having at least one cell wall which includes a transparent portion adjacent to an ECL chamber defined within the cell, a working electrode abutting the ECL chamber and in optical registration with the transparent portion, a counter electrode abutting the ECL chamber, a photodiode adjacent to and in optical registration with the transparent portion, and a magnetic field generating device operable to apply a magnetic field at the working electrode.

According to yet another aspect of the present invention an apparatus for the conduct of electrochemiluminescence measurements includes a cell having at least one cell wall which includes a transparent portion adjacent to an ECL chamber defined within the cell, a working electrode abutting the ECL chamber and in optical registration with the transparent portion, a counter electrode abutting the ECL chamber, and a photodiode adjacent to and in optical registration with the transparent portion, the photodiode having a detection sensitivity substantially limited to light having a wavelength in a range of 400 nm to 900 nm.

According to yet another aspect of the present invention an apparatus for the conduct of electrochemiluminescence measurements includes a cell having at least one cell wall which includes a transparent portion adjacent to an ECL chamber defined within the cell, a working electrode abutting the ECL chamber and in optical registration with the transparent portion, a counter electrode abutting the ECL chamber and having an aperture in optical registration with the transparent portion, a photodetector adjacent to and in optical registration with the transparent portion, and a magnetic field generating device, in registration with the aperture, operable to apply a magnetic field to the working electrode.

According to another aspect of the present invention an apparatus for the conduct of electrochemiluminescence measurements includes a cell having at least one cell wall which includes a transparent portion adjacent to an ECL chamber defined within the cell, a working electrode abutting the ECL chamber and in optical registration with the transparent portion, a counter electrode abutting the ECL chamber, a photodiode adjacent to and in optical registration with the transparent portion, a magnetic field generating device operable to apply a magnetic field to the working electrode, and a magnetic field detector, in registration with the magnet device.

According to another aspect of the present invention an apparatus for the conduct of electrochemiluminescence measurements includes a cell having at least one cell wall which includes a transparent portion adjacent to an ECL chamber defined within the cell, a working electrode abutting the ECL chamber and in optical registration with the transparent portion, a counter electrode abutting the ECL chamber, a photodiode, adjacent to and in optical registration with the transparent portion, for detecting electrochemiluminescence induced in an assay fluid in the ECL chamber and for producing an ECL signal representative of an intensity of the electrochemiluminescence, a storage device, coupled to the photodiode, in which a calibration signal representative of a calibration electrochemiluminescence may be stored, and a processor, coupled to the photodiode and to the storage device, operable to calculate an intensity value as a function of the ECL signal and the calibration signal.

According to another aspect of the present invention a cell for the conduct of electrochemiluminescence measurements includes a first base having a first interior surface, a planar working electrode positioned on the first interior surface, a second base having a second interior surface and having a transparent portion therein to allow light to pass therethrough, a planar counter electrode positioned on the second interior surface, the counter electrode having at least one opening therein to allow the light to pass therethrough in registration with the working electrode and the transparent portion of the second base, a gasket positioned between the working electrode and the counter electrode to define therebetween a cell volume, the volume communicating with the opening in the counter electrode, and a retaining device, coupled to the bases, wherein the interior surfaces of the bases are in opposing relationship to form the cell and wherein the second base includes a conduit through which fluid may be introduced into and removed from the cell volume.

According to another aspect of the present invention a cell for the conduct of electrochemiluminescence includes cell structural elements, a working electrode and a counter electrode, at least one of the structural elements having a transparent portion therein, wherein the working electrode is mounted on an interior surface of a structural element, a portion of the working electrode and the transparent portion of the at least one structural element defining, at least in part, a chamber for the conduct of electrochemiluminescence, the working electrode including the entirety of a continuous planar surface of the chamber and the portion of the working electrode and the transparent portion of the structural element being optically in registration with one another.

According to another aspect of the present invention a method for conducting an ECL measurement includes the steps of introducing an assay sample into an ECL chamber within a flow cell, simultaneously applying an electric field and a magnetic field to the assay sample in the ECL chamber, and measuring, through an electrically-shielded window defining a wall of said ECL chamber, electrochemiluminescence induced in the assay fluid in the ECL chamber while the electric field and the magnetic field are applied.

According to another aspect of the present invention a method for conducting an ECL measurement includes the steps of introducing an assay sample into an ECL chamber within a flow cell, simultaneously applying an electric field and a magnetic field to the assay sample in the ECL chamber, and measuring with a semiconductor photodetector electrochemiluminescence induced in the assay fluid in the ECL chamber while the electric field and the magnetic field are applied.

According to another aspect of the present invention a method for normalizing a plurality of ECL measurement instruments includes the steps of conducting an ECL measurement with a reference ECL measurement instrument upon a reference sample to produce a reference ECL signal, conducting an ECL measurement with a test ECL measurement instrument upon the reference sample to produce a test ECL signal, and calculating a correction transform function as a function of the reference ECL signal and the test ECL signal.

According to another aspect of the present invention an apparatus for the conduct of assay measurements includes a cell having at least one cell wall which includes a transparent portion adjacent to an ECL chamber defined within the cell, a working electrode abutting the ECL chamber and in optical registration with the transparent portion, a counter electrode abutting the ECL chamber, a first light detector, optically coupled to the ECL chamber and in optical registration with the transparent portion, for detecting electrochemiluminescence induced within the ECL chamber, a light source, optically coupled to the ECL chamber, for providing light to the ECL chamber, and a second light detector, optically coupled to the ECL chamber.

According to another aspect of the present invention an assay system includes a plurality of ECL modules and a controller device coupled to each of the plurality of ECL modules and operable to control an operation of each of the plurality of ECL modules.

According to another aspect of the present invention an assay system includes a plurality of ECL modules and a power supply coupled to each of the plurality of ECL modules and operable to supply electrical power to each of the plurality of ECL modules.

According to another aspect of the present invention an assay system includes a plurality of ECL modules and a sample introduction device coupled to each of the plurality of ECL modules and operable to supply a sample to each of the plurality of ECL modules.

According to another aspect of the present invention an assay system includes a plurality of ECL modules and a waste handling device coupled to each of the plurality of ECL modules and operable to receive waste from each of the plurality of ECL modules.

According to another aspect of the present invention an assay system includes a temperature-controlled enclosure and a plurality of ECL modules positioned within the temperature-controlled enclosure.

According to another aspect of the present invention an assay system includes an ECL module having an assay fluid outlet and an assay module having an assay fluid inlet coupled to the assay fluid outlet.

According to another aspect of the present invention an assay system includes an assay module having an assay fluid outlet and an ECL module having an assay fluid inlet coupled to the assay fluid outlet.

According to another aspect of the present invention an assay system includes an ECL module having a first assay fluid inlet and a first waste fluid outlet and an assay module having a second assay fluid inlet coupled to first assay fluid inlet and having a second waste fluid outlet coupled to the first waste fluid outlet.

According to another aspect of the present invention a modular ECL assay subsystem adapted for connection to and use with a power supply, a controller, and a fluid exchange system common to a plurality of the modular ECL subsystems includes a cell having at least one cell wall which includes a transparent portion adjacent to an ECL chamber defined within the cell, a working electrode abutting the ECL chamber and in optical registration with the transparent portion, a counter electrode abutting the ECL chamber, a light detector, optically coupled to the ECL chamber, for detecting electrochemiluminescence induced within the ECL chamber, a waveform generator coupled to at least one of the working electrode and the counter electrode and operable to generate an electric signal, a subsystem controller coupled to the waveform generator and operable to control an operation of the waveform generator, and an interface to the cell, coupled to each of the subsystem controllers, to the power supply, to the controller, and to the fluid exchange system, the controller being operable to control the subsystem controller, the power supply being operable to supply electrical power to the subsystem controller and the fluid exchange system being operable to provide an assay fluid to the cell and to receive a waste fluid from the cell.

BRIEF DESCRIPTION OP THE DRAWINGS

FIGS. 3A and 3B illustrate a flow cell according to an embodiment of the present invention;

Figure 1:
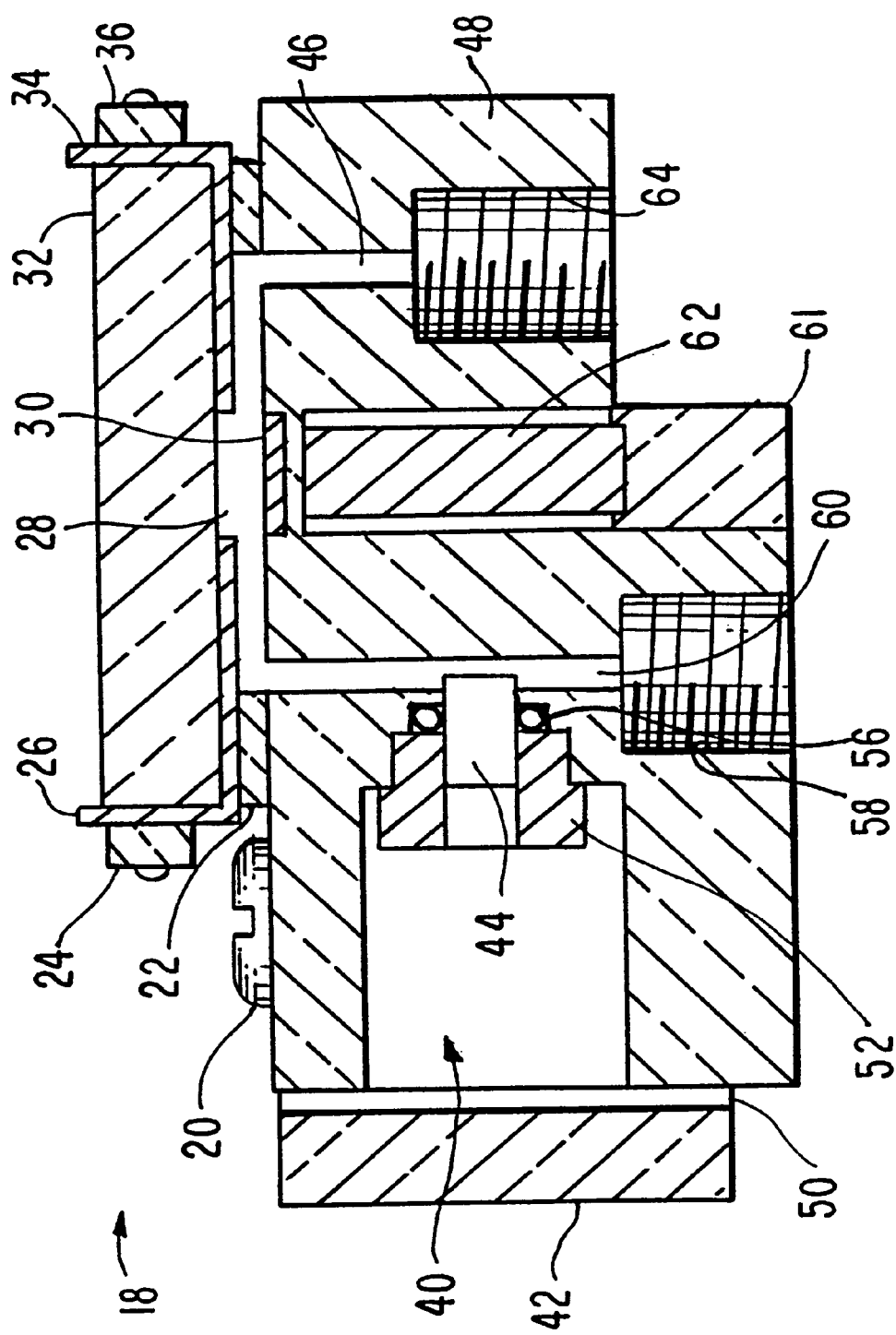
FIG. 1 illustrates a prior art flow cell.
Figure 2:
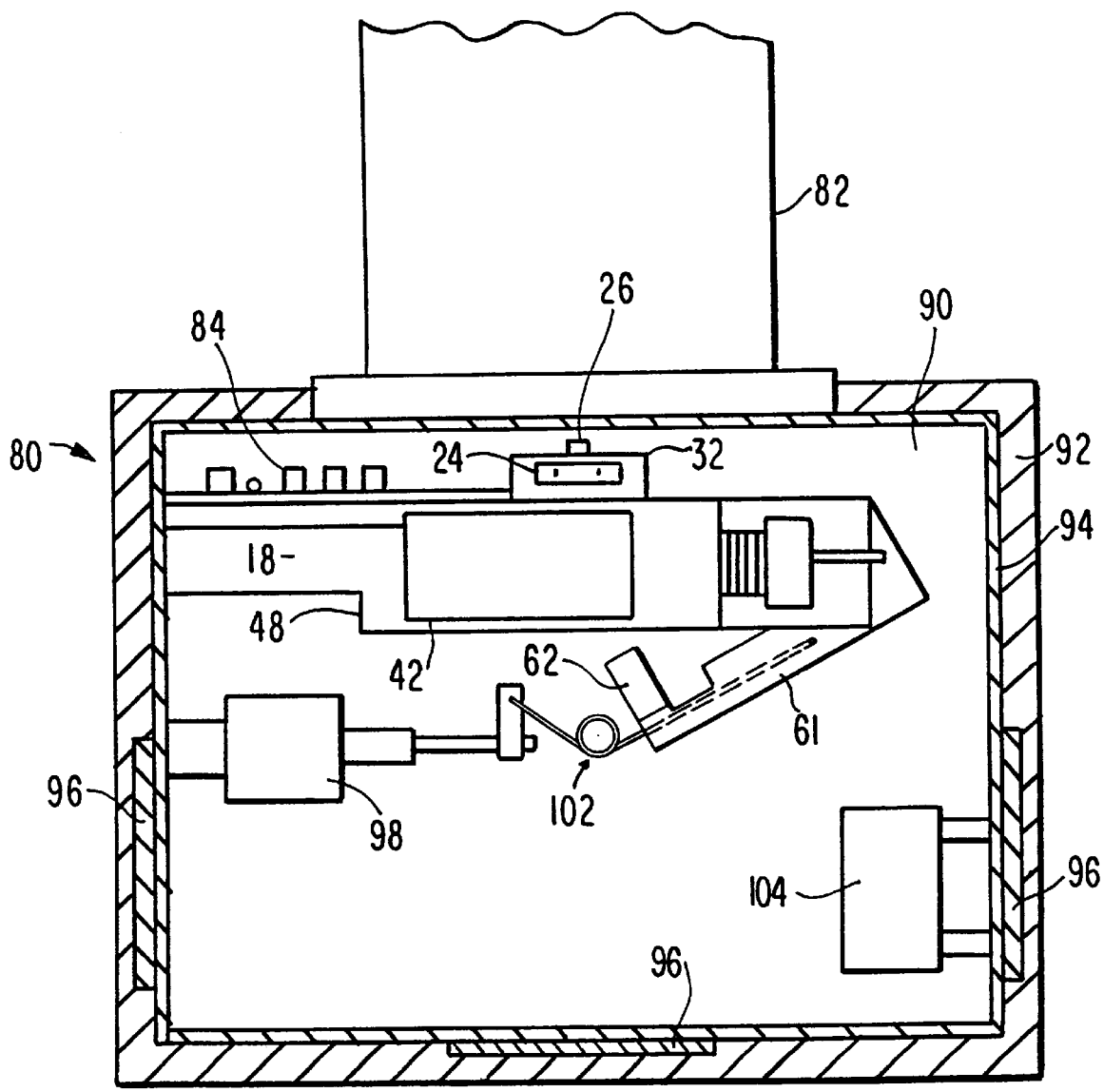
FIG. 2 illustrates a prior art ECL measurement apparatus.
Figure 5:
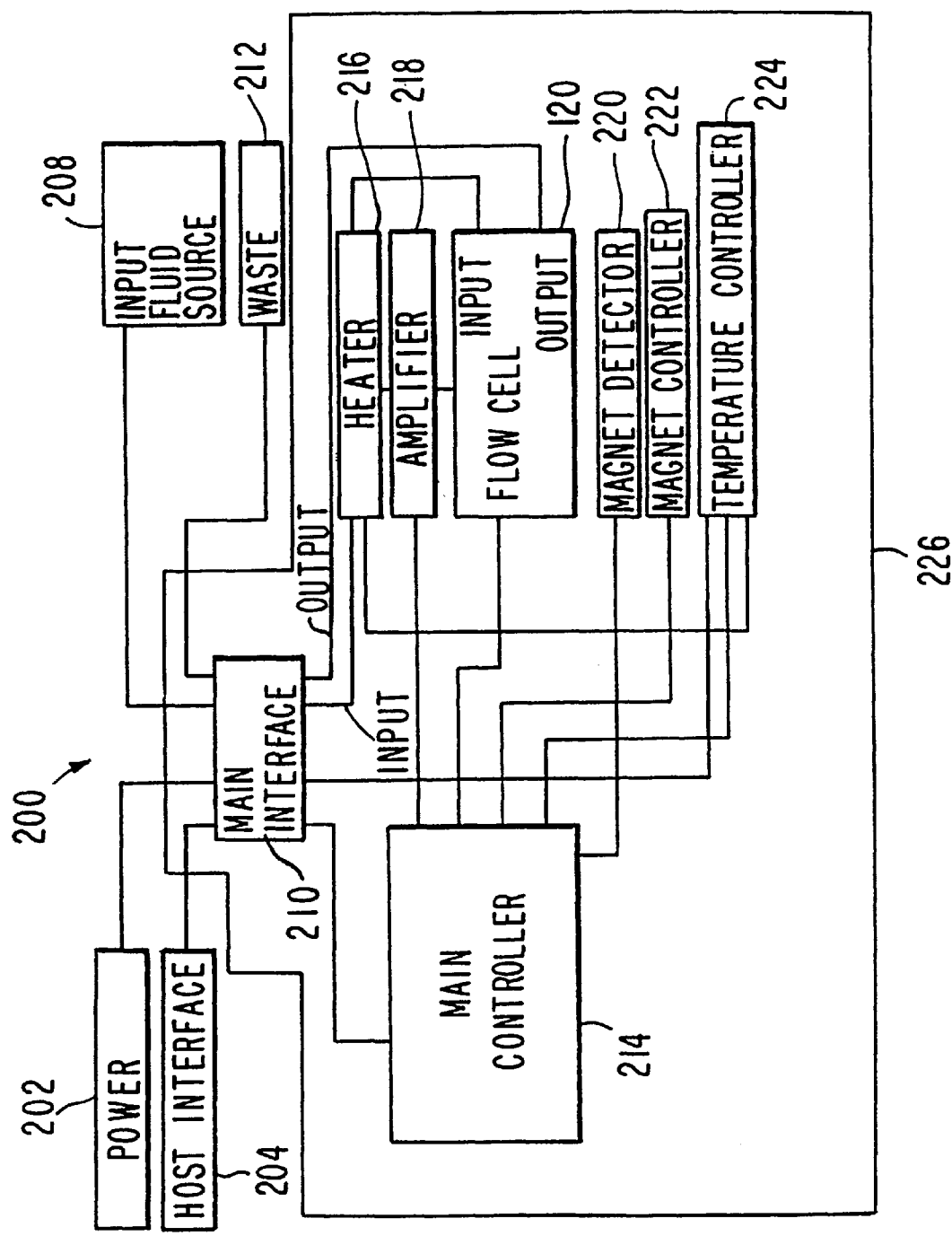
Figure 6:
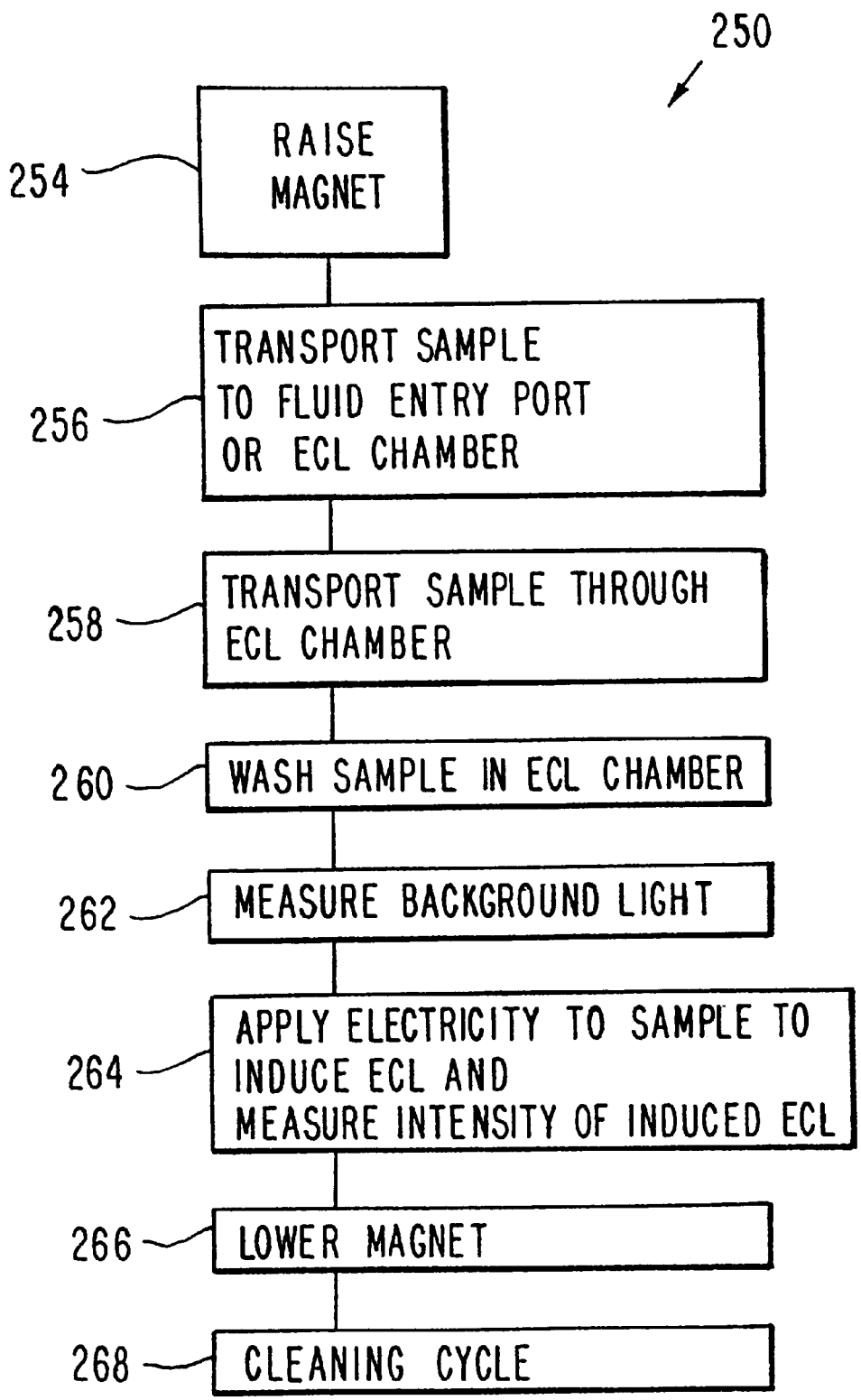
Figure 7:
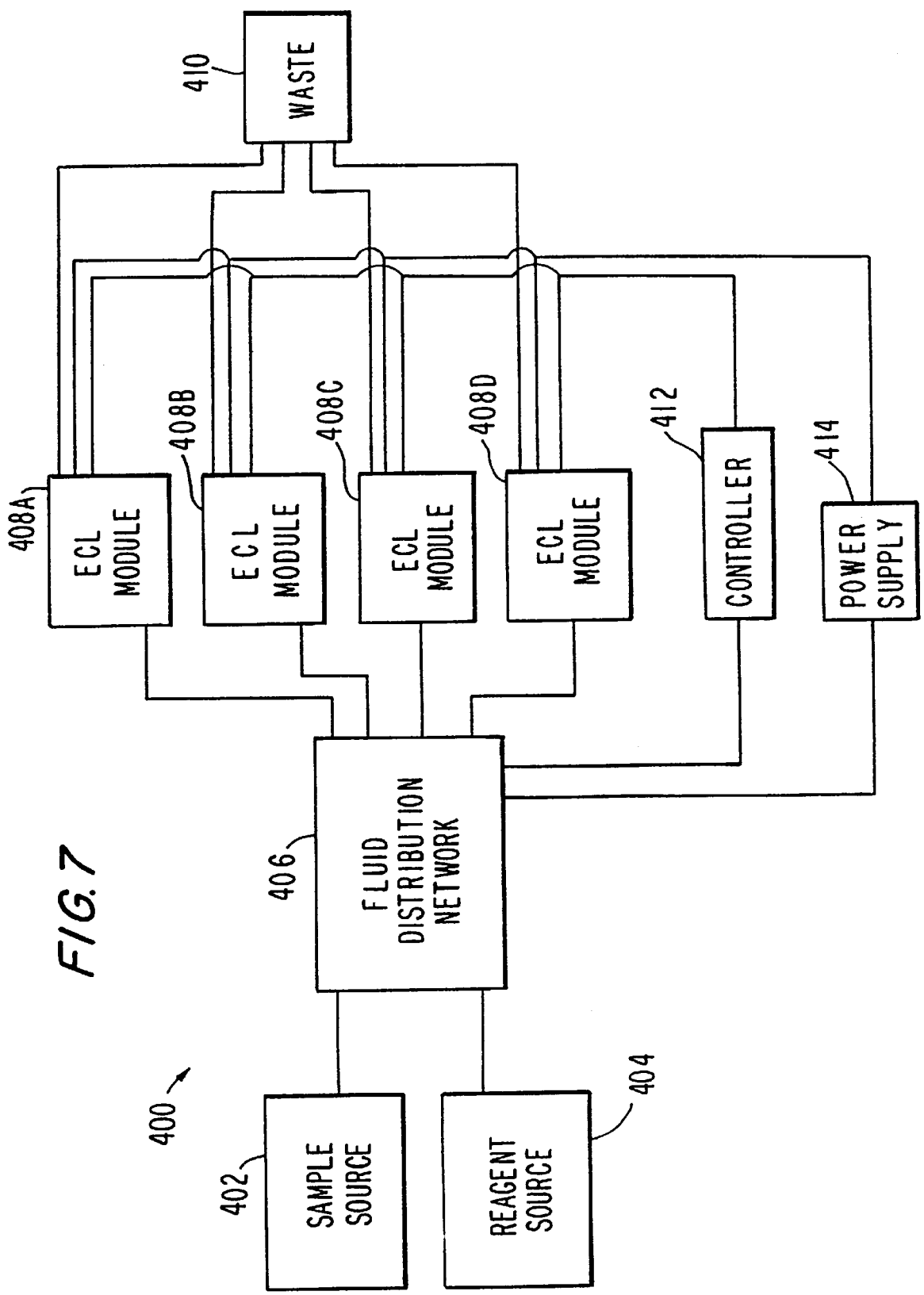
Figure 9A:
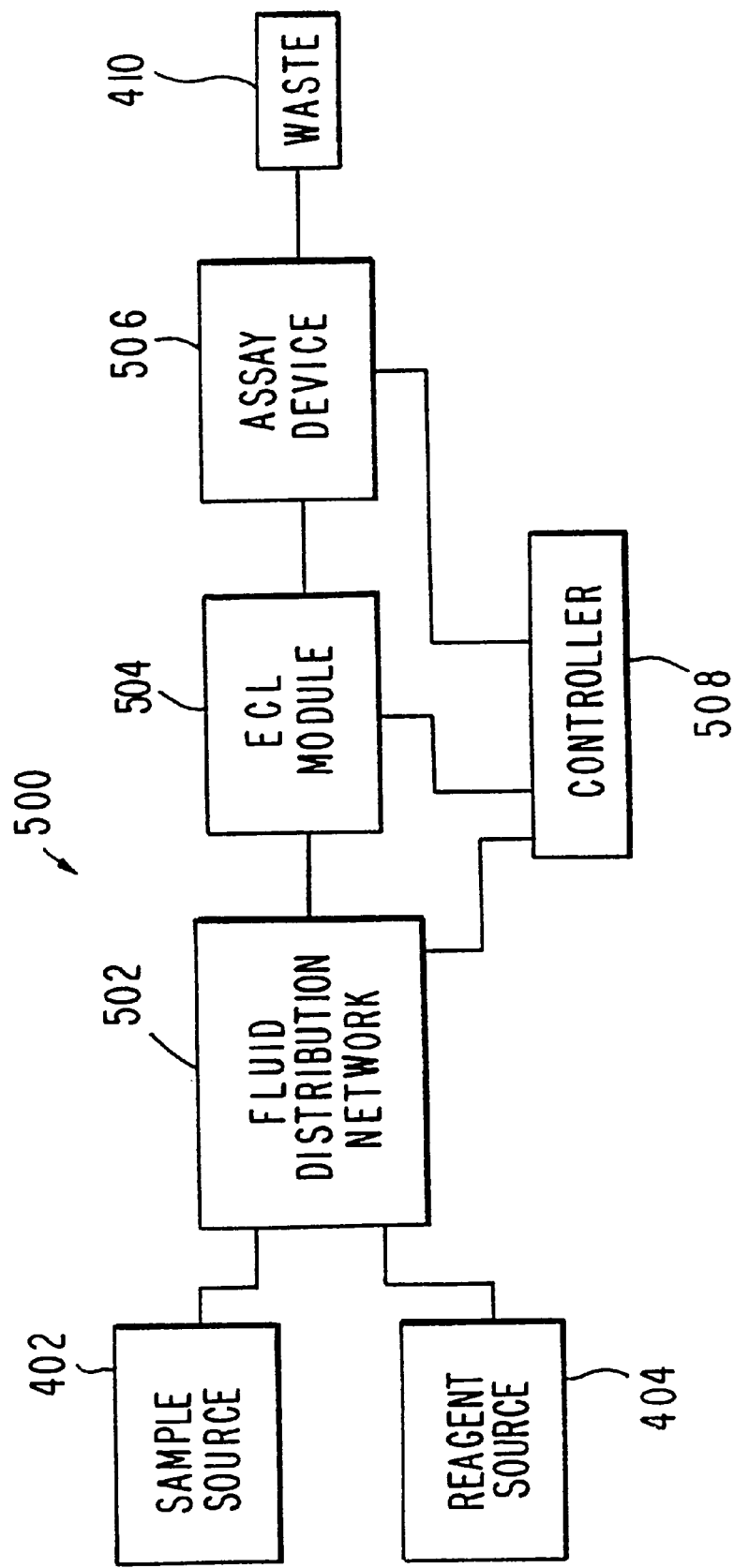
Figure 11:
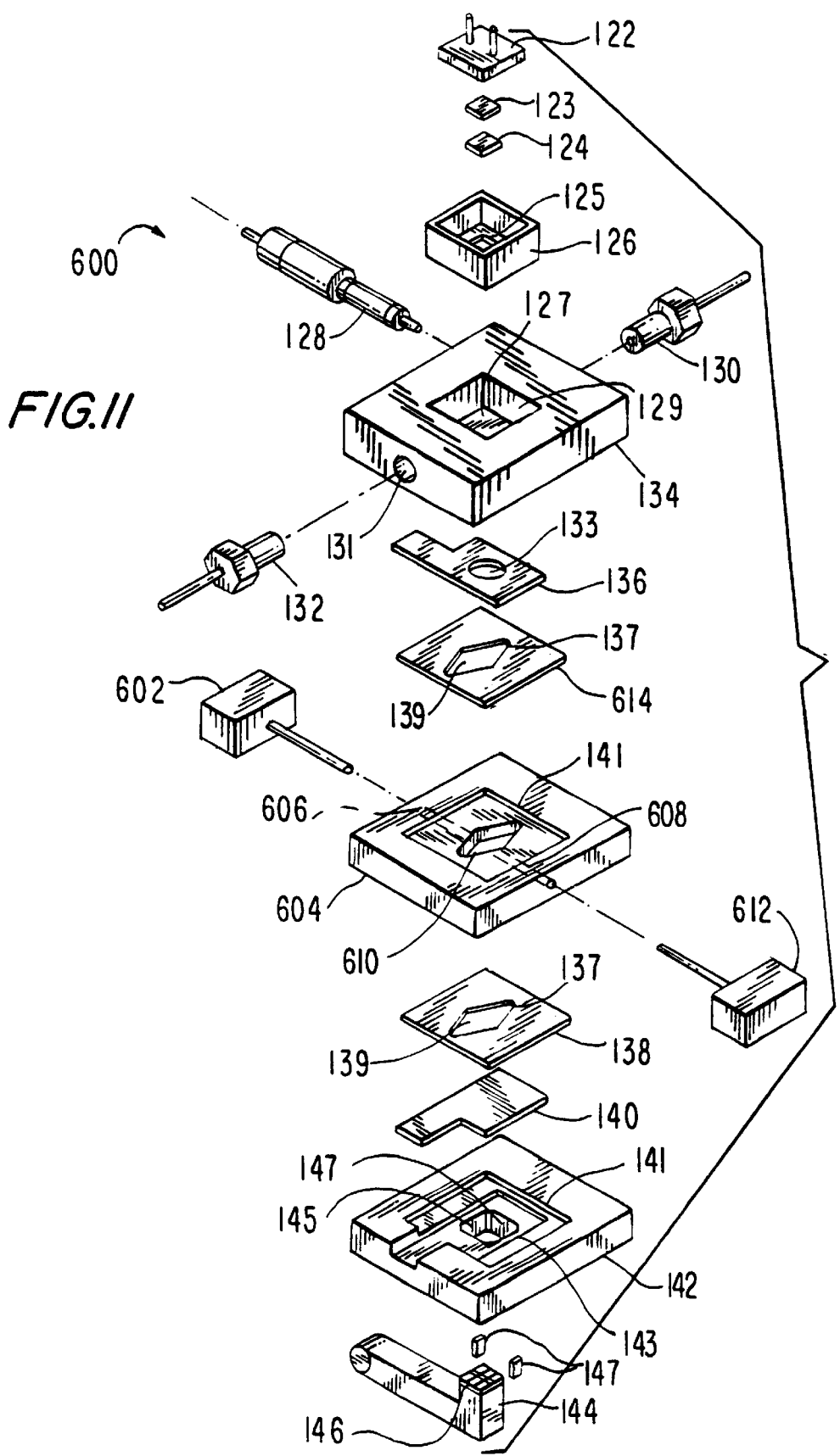

FIGS. 4A, 4B, 4C, and 4D illustrate a flow cell component according to an embodiment of the present invention;

FIG. 5 illustrates an ECL measurement apparatus according to an embodiment of the present invention;

FIG. 6 is a flow chart illustrating an ECL testing method according to an embodiment of the present invention;

FIG. 7 is a block diagram of an integrated system for ECL measurements according to an embodiment of the present invention;

FIGS. 8A and 8B illustrate components of an integrated system for ECL measurements according to an embodiment of the present invention;

FIG. 9A is a block diagram of an integrated system for ECL measurements according to an embodiment of the present invention;

FIG. 9B is a block diagram of an integrated system for ECL measurements according to an embodiment of the present invention;

FIGS. 10A, 10B, 10C and 10D illustrate components of an integrated system for ECL measurements and for measurements with other devices according to an embodiment of the present invention; and FIG. 11 illustrates a flow cell according to an embodiment of the present invention.

DETAILED DESCRIPTION OF THE PREFERRED EMBODIMENTS

The invention is in an ECL module capable of carrying out ECL measurements and capable of being integrated with other modules and/or instrumentation in a modular system. Advantageously, the ECL module is small, easy and inexpensive to manufacture, reliable and durable. The ECL module can be rapidly and efficiently incorporated into a variety of instruments specially-designed to serve particular markets, perform particular functions, or otherwise satisfy the requirements of specific applications. The ECL module dramatically reduces the time and cost required to create new ECL-based instruments.

Instruments incorporating an ECL module benefit from the standardization inherent in the module's design. Quality control testing, calibration, service, and upgrading of an instrument based upon an ECL module are greatly simplified since each process benefits from the interchangeable nature of the ECL module.

In the following the term transparent is defined as capable of transmitting any amount of light. In this sense, transparent matter may pass light fully or partially or it may be translucent. The term light refers to any electromagnetic radiation.

Objects in optical registration have a light path between them. A light path may include optical elements such as mirrors, lenses, prisms, optical fibers, gratings, apertures and other elements that may influence the properties or direction of light. A light path may also incorporate geometric alignment.

FIG. 3A illustrates an exploded view of a flow cell 120 according to the invention and FIG. 3B illustrates a cross-sectional view of flow cell 120 as assembled. Flow cell 120 comprises a light detector 122, an optical filter 123, a conductive window 124, a shield 126, a reference electrode 128, couplings 130 and 132, a cell component 134, a counter electrode 136, a gasket 138, a working electrode 140, a cell base 142, a pivot arm 144, magnet 146 and a magnet detector 147.

Light detector 122 is a sensitive light detection device, such as a semiconductor photodetector, which is tolerant of relatively high temperatures and can operate accurately in the presence of a magnetic field. Preferably, light detector 122 is sensitive to light in the 400–800 nm range, is physically small, e.g., 1"×1"x.5" or less, and comprises a silicon photodiode. In particular, IR-suppressing photodiode model #S1227-66BR, manufactured by Hamamatsu, is a preferred implementation of light detector 122. It is further preferred that light detector 122 be operable at ordinary electronic device voltages, e.g., within the approximate range of +/−12v, and not utilize the high voltages required by devices such as a photomultiplier tube, e.g., greater than +/−24 volts.

Light detector 122 may optionally include an optical filter as an integral component such as, for example, a thin film deposited on the light-collecting surface of detector 122. In particular, Hamamatsu's IR-suppressing photodiode model #S1227-66BR is considerably less sensitive to light of a wavelength greater than approximately 730 nm and, accordingly, demonstrates significantly improved accuracy and precision in detecting light emitted by ECL labels comprising Ru(bpy)$_3$ derivatives. Accordingly, an IR-suppressing light detector 122, e.g., one that inherently avoids the detection of infrared radiation, is preferred. Light detector 122 produces a light measurement signal as a function of the light incident upon it.

Optical filter 123 transmits light of certain wavelengths to light detector 122 while substantially preventing the transmittance of light of other wavelengths. Preferably, optical filter 123 comprises a thin film of optically filtering material that is coextensive with a light detecting area of light detector 122. Alternatively, filter 123 may comprise any optical component capable of passing certain wavelengths of light to light detector 122 and preventing other wavelengths of light from reaching light detector 122. As a further alternative, optical filter 123 may not be coextensive with light detector 122.

To maximize the operating efficiency of light detector 122, the transmittance characteristics of filter 123 are preferably matched to the wavelengths of the light emitted by an ECL label during an ECL assay. It is specifically preferred that filter 123 absorb light having a longer wavelength than that of the light emitted by the ECL label. Preferred embodiments of filter 123 include one or more of: i) a short pass filter having a transmittance of 600 nm light that is more than four times greater than its transmittance of 1000 nm light; ii) a short pass filter having a transmittance of 600 nm light that is more than four times greater than its transmittance of 800 nm light; and iii) a short pass filter having a transmittance of 600 nm light that is more than four times greater than its transmittance of 700 nm light, or a combination thereof. Optionally, filter 123 may be omitted from flow cell 120. Alternatively, filter 123 may be a short pass optical filter for passing light having a wavelength of less than 800 nm, more preferably less than 750 nm, and most preferably less than 700 nm.

In an alternate embodiment, light detector 122 comprises an avalanche photodiode detector or an array of light detectors, such as a CCD array, CID array, a photodiode array, and the like. By utilizing an array of light detectors and analyzing their corresponding respective light detection signals, different sources of light within flow cell 120 may be differentiated from each other.

Conductive window 124 is formed of a thin, light-transmitting, electrically-conductive material shaped to be coextensive with aperture 125. Alternatively, conductive window 124 is not coextensive with aperture 125. Preferably, window 124 includes a metallic mesh comprising copper, brass, or the like. Alternatively, window 124 may comprise a transparent, conductive material such as a thin film of indium-tin oxide deposited on a transparent substrate. It is further contemplated that window 124 may comprise an electrically conductive or otherwise electrostatically shielding configuration of a solid, liquid, gel, or gas. Window 124 shields light detector 122 from electrical noise that might adversely affect its performance; thus window 124 is electrically shielded. The light transmittance of window 124 should be greater than 40% and preferably is greater than 70%. It is most preferred that window 124 have a transmittance of greater than 85% for light emitted by an ECL label.

Where window 124 has been implemented as a mesh, it is preferred to size the apertures in the mesh relative to the type of electromagnetic radiation against which the mesh is to shield. For example, meshes having apertures of less than 1 mm, or more preferably less than 0.7 mm, or most preferably less than 0.3 mm, have been found to effectively shield against the apparent capacitive coupling between light detector 122 and one or more of working electrode 140 and counter electrode 136.

Shield 126 comprises a generally opaque configuration of electrically-conductive material, such as brass, aluminum or the like, preferably shaped like an open container. Shield 126 has an open top to accommodate installation of light detector 122 and a bottom surface having an aperture 125 adapted to accommodate conductive window 124. Optionally, aperture 125 is adapted to additionally accommodate optical filter 123. As a further option, shield 126 may include a top surface to thereby completely surround light detector 122. Alternatively, shield 126 may comprise an electrically-conductive, and preferably transparent, coating upon or within light detector 122 and, thus, window 124 and/or shield 126 may optionally be omitted.

As a further alternative, shield 126 may be omitted if light detector 122 is of a type not adversely affected by capacitive interference or electric fields. Shield 126 may have a bottom surface which both conducts electricity and transmits light but omits any aperture, e.g., has a continuous bottom surface. Of course, shield 126 and conductive window 124 may be contiguous, e.g., a brass shield having a perforated bottom surface.

An optical epoxy, such as a multi-part epoxy, may be used to bond together light detector 122, filter 123, window 124, shield 126, and cell component 134 or any subset thereof. Preferably, the optical epoxy fills in all the gaps, if any, between the elements, thereby ensuring an optional path between cell component 134 and light detector 122 which omits solid/air and liquid/air interfaces.

Couplings 130 and 132 are conventional fluid couplings for connecting fluid-carrying tubes to cell component 134. Reference electrode 128 is an ECL reference electrode for detecting the voltage level of an assay sample. Preferably, reference electrode 128 includes a ceramic or glass frit along with an ionic transfer medium, and engages in only a minimal fluid transaction with the assay sample. It is additionally preferred that electrode 128 be entirely replaceable and modularly renewable. The invention allows for increased lifetime of the ECL cell by improved design of the reference electrode. In one embodiment, the volume of the medium in the reference electrode is greater than 0.3 cubic inches. Alternatively, the reference electrode may be omitted.

Cell component 134 is comprised of a rigid material and is shaped to include a central well 129, coupling opening 131 to accommodate coupling 132, another coupling opening (not shown) to accommodate coupling 130, a reference electrode opening (not shown) to accommodate reference electrode 128, and a counter electrode groove (not shown) to accommodate counter electrode 136. As shown, the box-shaped central well 129 is adapted to accommodate shield 126, window 124, and, optionally, optical filter 123. Preferably, cell component 134 comprises a durable, transparent and chemically inert material such as plexiglass, acrylic, polymethyl methacrylate, or the like. Alternatively, component 134 may be comprised of a non-transparent material except for at least some of its volume between its lower surface (which includes the counter electrode groove) and central well 129. At minimum, base 127 of central well 129 should provide a transparent zone (e.g., an optical pathway or window) between ECL chamber 139 and light detector 122 through which light generated in ECL chamber 139 may pass.

Counter electrode 136 comprises a conductive electrode having one or more openings 133 therein. Opening 133 is preferably circular; but, may instead be oval, triangular, rectangular, diamond-shaped, trapezoidal or another shape. Preferably, counter electrode 136 is comprised of a metal, such as nickel, stainless steel, gold or platinum. Counter electrode 136 may comprise a mesh or a screen. Counter electrode 136 is preferably shaped to fit a counter electrode groove in component 134 for secure mounting. For example, counter electrode 136 may be "L"-shaped, as shown, rectangular in shape, "T"-shaped or the like. The "L"-shape and "T"-shape are particularly advantageous in that one "arm" of the configuration may be positioned to extend beyond the periphery of component 142 to provide an electrical contact point for the provision of electrical energy.

Gasket 138 comprises a conventional gasket material (e.g., silicone rubber) which is preferably pliable and elastomeric so as to most effectively provide fluid-tight seals to the other surfaces that define ECL chamber 139. To reduce lateral deformation of the gasket during compression, gasket 138 is most preferably formed from a material with a durometer number of greater than 60 Shore A points hardness. By reducing lateral deformation, it is possible to maintain a more precise control over the lateral dimensions of ECL chamber 139 and thereby improve the precision of ECL measurements.

In an alternate embodiment, gasket 138 comprises an elastomeric material and another material which has a greater lateral stiffness than the elastomer. For example, gasket 138 may be formed from a layered material comprising a laterally stiff middle layer, such as nylon or acrylic, that resists lateral deformation and a pair of elastomeric top and bottom layers that provide fluid-tight seals. Additionally, the middle layer could comprise a continuous solid, a network of fibers, or a mesh. In a gasket comprising a network of fibers or a mesh, the network or mesh is preferably oriented so that its longitudinal axis is substantially perpendicular to the narrowest dimension of the gasket.

Gasket 138 includes an opening 137 that is preferably shaped to allow an even and uniform fluid flow through ECL chamber 139, especially over the surface of working electrode 140. Preferred shapes for opening 137 include a parallelogram and a diamond. Opening 137 defines sides of ECL chamber 139.

Working electrode 140 comprises a conductive electrode, preferably made of a metal, such as gold or platinum, formed in a planar sheet. Preferably, electrode 140 is shaped to fit within working electrode groove 143 for secure mounting therein. For example, electrode 140 may be "L"-shaped as shown, rectangular in shape, "T"-shaped or the like. The "L"-shape and "T"-shape are particularly advantageous in that one "arm" of the configuration may be positioned to extend beyond the periphery of component 134 to provide an electrical contact point for the provision of electrical energy.

Cell base 142 comprises a rigid base material having an opening 145 extending therethrough, a working electrode groove 143 adapted to accommodate working electrode 140, and a gasket groove 141 adapted to accommodate gasket 138. Preferably, cell base 142 comprises a durable and chemically inert material, such as plexiglass, acrylic, polymethyl methacrylate, or the like. As shown, opening 145 preferably has the cross-section of a square with rounded corners but, alternatively, may have any shape suitable to accommodate magnet 146 and/or pivot arm 144. Optionally, opening 145 is omitted from cell base 142.

Preferably, magnet detector 147 extends into or near opening 145. In another embodiment, magnet detector 147 is attached to the lower surface of base 142 or is incorporated into base 142. Magnet detector 147 preferably comprises a conventional magnetic field detector such as a magnetometer and provides an output signal indicating the presence, absence, or proximity of magnet 146 and/or pivot arm 144. In an especially preferred embodiment, magnet detector 147 comprises one or more Hall-effect sensors or the like. Alternatively, magnet detector 147 is omitted from cell 120.

Cell component 134 and cell base 142 may be held together by a conventional retaining device incorporated into, affixed to, or associated with one or both of component 134 and base 142. Such a retaining device may comprise screws, rivets, bolts, pins, clips, clamps, elastic fasteners, adhesives, tapes, fasteners, and the like.

Preferably, working electrode 140 is mounted in working electrode groove 143 without any adhesive or permanent fastener. Instead, electrode 140 fits precisely within groove 143 and is held in place by gasket 138 sandwiched between cell component 134 and cell base 142. As a result, working electrode 140 is readily removed and replaced. By avoiding the use of an adhesive or other fixing agent to secure electrode 140, the process for manufacturing cell 120 is simplified considerably and the useful lifetime of cell 120 is substantially increased. The working electrode 140 is thus removably fitted into the cell. The cell of the invention can have a useful lifetime greater than 10,000 assay measurements; preferably this lifetime exceeds 25,000 assay measurements; more preferably, the lifetime of the cell exceeds 50,000 assay measurements; even more preferably, the lifetime exceeds 100,000 measurements; most preferably the lifetime of the cell exceeds 1,000,000 assay measurements.

Opening 137 in gasket 138, portions of working electrode 140 and counter electrode 136, both defined by gasket 138, and a portion of cell component 134 provide the boundaries for ECL chamber 139. Together, these elements also define a fluid path through ECL cell 120. It should be appreciated that opening 137 is positioned such that the fluid path does not include any seam between working electrode 140 and cell base 142.

Magnet 146 is a conventional magnet device, preferably a permanent magnet having a generally square shape, and is affixed to pivot arm 144. Alternatively, magnet 146 may comprise an electromagnet or the like. Pivot arm 144 is a generally rigid pivot arm configured to position magnet 146 within opening 145. At opening 145, magnet 146 may removably be positioned to touch working electrode 140 or may be positioned near thereto.

As shown in FIG. 3B, the registration of working electrode 140, opening 137, opening 133, transparent base 127, aperture 125, conductive window 124, optical filter 123 and light detector 122 is an important feature of the invention. Proper registration of these elements ensures optimal transmittance of light from the vicinity of working electrode 140 to light detector 122. Additionally, registration of magnet 146 and opening 145 with working electrode 140 allows for the precise and efficient application of magnetic energy at working electrode 140. Such magnetic energy is used to attract magnetic particles from an assay sample to working electrode 140 where electrochemiluminescence may be induced. Preferably, opening 133 itself functions as an optical element that defines the region of working electrode 140 and ECL chamber 139 from which induced electrochemiluminescence may propagate to light detector 122. Per design, counter electrode 136 may block undesired light generated in certain regions of ECL chamber 139. Preferably, the size and shape of the counter electrode aperture 133 is designed to maximize collection of light emitted from those regions of the working electrode 140 where magnetic beads have been deposited and minimize collection of light emitted from other regions of the working electrode 140.

Additionally, precise registration of opening 133 and magnet 146 is particularly important to maximize the amount of luminescence attributable to the desired reaction (vs. luminescence attributable to ancillary reactions) that is incident upon light detector 122. The strength and shape of the magnetic field produced by magnet 146 defines the region in which any material attracted by the magnetic field, e.g., magnetic beads, comes to rest. Preferably, opening 133 is sized and shaped to allow light emitted by or near such materials collected by magnet 146 in the vicinity of working electrode 140 to reach light detector 122 while minimizing the amount of light generated in other regions that reaches light detector 122. Accordingly, light detector 122 should be sized relative to opening 133 (or vice versa to ensure that the desired electrochemiluminescence is collected. Preferably the working area of light detector 122 is slightly larger than the cross sectional area of the light cone generated at the electrode and emitted through aperture 133.

FIGS. 4A, 4B, 4C, and 4D illustrate detailed views of cell component 134. FIG. 4A is a cross-sectional view of cell component 134 taken along the line 4A—4A of FIG. 4B. FIG. 4B is a top view of cell component 134. FIG. 4C is a cross-sectional view of cell component 134 taken along the line 4C—4C of FIG. 4B. FIG. 4D is a bottom view of cell component 134.

FIG. 4A illustrates a side cross-sectional view of cell component 134 and particularly depicts a central well 129, coupling openings 180 and 131, fluid ports 182 and 186, and a counter electrode groove 184. Central well 129 preferably has a cross-section compatible with that of light detector 122 and shield 126 (see FIG. 3A), e.g., rectangular as shown, and has a depth of approximately 75% of the depth of component 134. By embedding light detector 122 in central well 129, light detector 122 is positioned in close proximity to ECL chamber 139 and working electrode 140. Such proximity facilitates efficient light detection. In a preferred embodiment of assembled cell 120, the distance between light detector 122 and working electrode 140 is less than 2.2 mm. As shown, a portion of cell component 134 separates ECL chamber 139 from central wall 129; in a preferred embodiment, the thickness of this material is less than 1.3 mm.

Since interfaces in an optical path between materials (e.g., a plastic/air interface), interface between phases (e.g., a liquid/solid, solid/gas, or liquid/gas) or between materials with different refractive indices, may impede light transmission, cell 120 is designed to avoid or minimize such interfaces. In particular, the optical path between light detector 122 and ECL chamber 139 preferably avoids any interfaces that includes air, e.g., an air gap. To provide optimal optical coupling among elements in the optical path between detector 122 and chamber 139, optical adhesives and epoxies, index matched liquids, and index matched compliant materials, and the like are utilized to eliminate air gaps. Such optical coupling materials are especially useful in implementing a mesh as shield 124 (see FIG. 3A), since the optical coupling materials displace gas existing in the interstitial spaces between elements of the mesh. The use of optical coupling materials to eliminate air gaps has improved optical efficiency by as much as 40%. In a preferred embodiment, all cell elements and optical coupling materials forming the optical path between detector 122 and chamber 139 have refractive indices between 1.3 and 1.6, while refractive indices between 1.45 and 1.55 are especially preferred.

The light collection efficiency of cell 120 is a function of several factors such as, i) the strength, shape and placement of magnet 146; ii) the size, shape and position of opening 133; iii) the transmittance of window 124; iv) the distance between light detector 122 and ECL chamber 139; v) the efficiency of optical coupling among materials within the optical path; vi) the size and placement of light detector 122; vii) the properties of optical filter 123 and viii) cell geometry, e.g., the alignment of and distance between elements that comprise the optical path. Light collection efficiencies greater than 40% is preferred; efficiency greater than 50% is more preferred.

Coupling opening 180 is adapted to receive coupling 130 and coupling opening 131 is adapted to receive coupling 132. Counter electrode groove 184 is adapted to receive counter electrode 136. A tube in component 134 connects coupling opening 180 and fluid port 182. Another tube in component 134 connects coupling opening 131 and fluid port 186. Fluid ports 182 and 186 are positioned to allow fluid to flow from one port to the other through the ECL chamber 139 defined by opening 137 in gasket 138 (sides), working electrode 140 (bottom), counter electrode 135 (top), and circular hub 188 of cell component 134 (top). The longitudinal ends of opening 137 align with ports 182 and 186.

FIG. 4B illustrates a top view of cell component 134 and particularly depicts central well 129. Central well 129 is adapted to receive shield 126 and conductive window 124.

FIG. 4C illustrates a side cross-sectional view of cell component 134 and particularly depicts a reference electrode opening 190. Opening 190 intersects the tube connecting coupling opening 180 and fluid port 182. Reference electrode opening 190 is adapted to receive reference electrode 128.

FIG. 4D illustrates a bottom view of cell component 134 and particularly depicts counter electrode groove 184 and circular hub 188. The surface of circular hub 188 is preferably flat and flush with the bottom surface of cell component 134. Hub 188 is preferably integral to component 134 and is adapted to fit exactly within opening 133 of counter electrode 136. Hub 188, along with that portion of component 134 between hub 188 and central well 129 provide an optical pathway or window through which light may travel.

FIG. 5 illustrates an apparatus 200 incorporating an ECL measurement module 226 according to an embodiment of the present invention. Module 226 comprises a main interface 210, a main controller 214, a heater 216, an amplifier 218, a flow cell 120, a magnet detector 220, a magnet controller 222, and a temperature controller 224. Also shown are a power source 202, a host interface 204, an input fluid source 208, and an outlet for waste 212. Module 226 is preferably housed within a light-tight enclosure.

Main interface 210 is preferably the only interface for apparatus 210 and may consist of multiple individual interfaces (e.g. connectors) suitable for multiple connections. Interface 210 preferably includes removable connections to power source 202, host interface 204, input source 208, and outlet 212. Since such connections are removable, module 226 may be easily replaced as a single operational module. In addition, the modular design of the apparatus 226 allows for its incorporation into a variety of other instruments through connections to main interface 210. Preferably, the multiple connectors of main interface 210 are grouped such that the connections may be engaged or disengaged together in a single procedure. It is an important feature of this invention that the connectors can be engaged or disengaged readily, and in some embodiments, without fully interrupting the function of the device (e.g. "hot-swapping"). Preferably, fluid connectors incorporated into main interface 210 are self-sealing on disengagement and/or self-opening on engagement to prevent leakage of fluid or fluid path obstruction.

Main controller 214 is a control device, such as microcontroller PIC 16C65 by Microchip or the like, for controlling the basic operation of module 226 in response to commands from an external host (not shown). Main controller 214 is coupled to main interface 210, amplifier 218, flow cell 120, magnet detector 220, magnet controller 222, and temperature controller 224. Alternatively, main controller 214 may include a waveform generator such as a voltage source, a current source, a power supply, a potentiostat, or the like. Preferably, such a waveform generator is controllable and may be externally controllable, e.g. by an external control device. Preferably, such a waveform generator may be controlled so as to generate waveforms of any shape, including steps, ramps, ramp-and-holds, sinusoids, and/or any combination of the abovementioned waveforms. The waveform is optionally repeated multiple times. Upon receiving commands from an external host connected to host interface 204 through main interface 210, main controller 214 issues appropriate commands to, and may control the supply of power to, constituent parts of module 226. Preferably main controller 214 comprises a programmable timing controller, such as an electro-mechanical control device and, alternatively, may comprise a microprocessor-based control system. Optionally, controller 214 comprises a storage device, such as a semiconductor memory, magnetic storage media, optical storage media, magneto-optical storage media, and the like.

Amplifier 218 is an amplifier with controllable gain for amplifying the light measurement signal produced by light detector 122. Preferably, amplifier 218 has a gain of between 1 and 8000. The light measurement signal produced by light detector 122, a part of flow cell 120, may be amplified by amplifier 218 in accordance with a control signal provided by main controller 214. Optionally, the light measurement signal or an amplified version thereof is provided to main controller 214. Amplifier 218 is preferably directly connected to the output of light detector 122.

Flow cell 120 is the flow cell of FIG. 3 as previously described. Electrical energy is provided to cell 120 by main controller 214. In particular, the electrical energy may be generated by a waveform generator included in main controller 214.

Magnet detector 220 detects the positioning of magnet 146 and, in particular, whether magnet 146 is or is not proximate working electrode 140. Alternatively, magnet detector 220 may simply detect the positioning of pivot arm 144. Detector 220 provides an output signal to main controller indicative of the position of magnet 146. Magnet detector 220 may optionally be incorporated into flow cell 120. Magnet detector 220 is shown in FIG. 3A as magnet detector 147.

Magnet controller 222 is a control device, responsive to operational control signals from main controller 214 for controlling the positioning of magnet 146. Preferably, magnet controller 222 is an electro-mechanical device for positioning pivot arm 144. It is further preferred that proper operation of controller 222 and arm 144 are verified by reference to an output signal of magnet detector 220.

Heater 216, coupled to temperature controller 224, is a conventional controlled heating device for heating input fluid to be introduced into flow cell 120. Temperature controller 224 is a conventional temperature controller for controlling the operation of heater 216 and responding to control signals from main controller 214. Controller 224 receives power from power source 202 via main interface 210 and, preferably, controls the flow of power to heater 216. Controller 224 may include temperature sensors to determine the temperature of input fluids or, alternatively, such sensors may be incorporated into heater 216. Optionally, heater 216 and/or temperature controller 224 may be omitted.

In operation, fluid supplied from input fluid source 208 via main interface 210 may be heated by heater 216 and provided to an input of flow cell 120, specifically coupling 132. Coupling 132 transfers the input fluid through coupling opening 131 to fluid port 186 and into ECL chamber 139. Main controller 214 controls magnet controller 222 to position magnet 146 in proximity to working electrode 140. Magnet detector 220 provides a signal to main controller 214 indicative of the positioning of magnet 146.

Main controller 214 applies electrical energy to working electrode 140 and counter electrode 136 to cause the input fluid to electrochemiluminesce. Reference electrode 128 detects a reference voltage in the input fluid and provides a corresponding reference voltage signal to main controller 214. Main controller 214 adjusts its application of electrical energy to working electrode 140 and counter electrode 136 as a function of the reference voltage signal.

Light detector 122 detects the induced electrochemiluminescence and supplies a light measurement signal to amplifier 218 for amplification. Amplifier 218 provides the original or amplified signal to main controller 214 which routes same to main interface 210 for output to the host interface 204 and acquisition by the host (not shown).

The input fluid is pumped through ECL chamber 139 into fluid port 182 and coupling 130 via coupling opening 180. The expelled fluid travels through main interface 210 to outlet 212. Throughout the process, power source 202, connected to main interface 210, provides the power needed by module 226. Through main interface 210 and host interface 204, main controller 214 may be controlled by an external host to process input sample fluids at specific temperatures, with specific patterns of electrical energy, and with or without the application of a magnetic field.

FIG. 6 provides a flow chart illustrating a preferred method 250 of ECL test measurement according to an embodiment of the present invention. According to method 250, in step 254, main controller 214 controls magnet controller 222 to control pivot arm 144 to raise magnet 146 into a position in close proximity to working electrode 140. Magnet detector 220 detects the position of the magnet to verify its proper placement. In the next step 256, an assay sample is transported to the fluid entry port of the flow cell, e.g., fluid port 186, having already passed through main interface 210 and heater 216. Thereafter, in step 258, the assay sample is pumped through ECL chamber 139 and materials in the assay sample are collected by the magnetic field of magnet 146 at working electrode 140.

A washing fluid, such as an assay buffer, is then pumped through ECL chamber 139 at a relatively high speed in step 260 to wash the materials collected by magnet 146. Thereafter, an assay fluid, such as an assay buffer, may be pumped through ECL chamber 139 at a relatively low speed. In step 262, main controller 214 controls light detector 122, possibly through amplifier 218, to detect a background level of light present in ECL chamber 139.

In the subsequent step 264, main controller 214 applies electricity to the sample collected at working electrode 140. An electric field is created between counter electrode 136 and working electrode 140. Preferably, the electric field is generated by stepping the potential at the working electrode to 1.4 V (vs. Ag/AgCl) and holding such voltage for a period of two seconds. The collected sample is thereby induced to electrochemiluminesce and the intensity of the resulting light is measured by light detector 122. Detector 122 provides a light measurement signal to main controller 214 via amplifier 218. Main controller 214 may modulate the strength of the applied electric field.

The implementation of a light detector 122 that operates accurately in the presence of a magnet field is clearly advantageous. The magnetic field concentrates sample materials at the surface of working electrode 140 and prevents their dispersion. With magnet 146 raised, ECL measurements may be made successfully under conditions of moderate to strong fluid flow without loss of sample. In addition, by measuring ECL under conditions of flow, reagents consumed by the ECL process can be replenished during the measurement.

In step 266, main controller 214 controls magnet controller 222 to cause pivot arm 144 to be retracted, lowering magnet 144 away from working electrode 140. Thereafter, in step 268, a cleaning and/or conditioning cycle occurs. Preferably, cleaning fluid and/or air bubbles are pumped through the flow cell during the cleaning cycle.

In the apparatus of the present invention, a magnet detector, e.g., a Hall-sensor, independently verifies the consistencies of the magnetic field applied to fluid within ECL chamber 139. Accordingly, magnetic beads need not be used to calibrate this apparatus. ECL labels dissolved in solution or otherwise not affiliated with materials influenced by a magnetic field can be used as standards to measure the ability of cell 120 to induce and detect electrochemiluminescence independently of the magnetic field. Since magnetic bead-based calibration standards with well-defined characteristics are difficult and expensive to manufacture reliably and may be unstable during long-term storage, it is advantageous that cell 120 may be calibrated without the utilization of such standards. Independent verification of the magnetic field with a magnet detector and utilization of an ECL standard not based on magnetic beads facilitates diagnostic methods that distinguish between magnetic field failure and electrochemiluminescence induction/detection failures. Such diagnostic precision considerably simplifies service and repair of an instrument.

The invention includes integrated systems for measuring analytes. These systems include one or more integrated ECLM modules as described above. The system may include a sample introduction device, power supplies, controllers, and electrical mechanical and fluid connections to the modules, a case or physical support and a user interface. The sample introduction device, power supplies, controllers, and electrical mechanical and fluid connections to the modules, a case or physical support and user interface may or may not be shared by a plurality of ECL modules. The ECL modules in these systems are designed to be integrated with other instrumentation that generates samples benefiting from diagnostic testing (e.g. chemical reaction chambers, bioreactors, biomolecule synthesizers, water collection systems, lithographic processors) without undue effort, cost or expenditure of time.

FIG. 7 illustrates an assay system 400 with multiple ECL modules 408A–D. System 400 includes a sample source 402, a reagent source 404, a fluid distribution network 406, ECL modules 408A–D, waste repository 410, controller 412, and power supply 414. As shown, fluid distribution network 406 is coupled to each of sample source 402, reagent source 404, ECL modules 408A–D, controller 412 and power supply 414. ECL modules 408A–D are each further coupled to waste repository 410, controller 412 and power supply 414. All connections to ECL modules 408A–D, besides physical supportive connections (not shown), occur through the respective main interface 210 (FIG. 5) of each. System 400 in whole, or in part, may be enclosed within a temperature-controlled environment. In an alternative embodiment, assay system 400 includes a single ECL module 408A, thus omitting ECL modules 408A, 408B and 408C. System 400 can be configured to accommodate any number of ECL modules 408. In hand-held or portable versions of system 400 power supply 414 may comprise a battery, fuel cell, one or more solar panels, or the like.

Sample source 402 comprises a conventional device for providing one or more assay samples. For example, source 402 may include one or more sample probes, pipettes, pumps, valves, tubing, containers for samples, meters, flow control devices, sample preparation devices, sample processing devices and other apparatus, or a combination thereof. Such sample processing devices may include filters, mixing chambers, reaction chambers and the like. Source 402 may also include, for example, multi-well plates, cartridges, test tubes and vacuum blood draw tubes. A cartridge may include a filtration membrane for filtering blood and may also contain other analytical components (e.g. ion selective electrodes, oxygen electrodes). Source 402 may comprise a system for handling and/or moving sample containers, e.g., multi-well plate stacking devices, tube carousels or racks, and automated sample delivery systems such as conveyer belts and robotic systems. Source 402 may include identification (e.g. bar codes or magnetic strips) devices to identify samples. In addition, source 402 may comprise, e.g., a separation device, such as a chromatography instrument or an electrophoresis instrument. Still further, source 402 may include a network of analytical devices, such as a chemical reactor, a protein sequencer, a separation device, a bioreactor, a chemical analysis instrument, or the like. Control of such systems may be implemented through controller 412 via a connection (not shown) or by another control device (not shown).

In an alternate embodiment, source 402 is the output stream of another analytical device, e.g., a device for the separation of materials, such as an HPLC or other chromatographic systems, a chemical reaction chamber, a cell culture chamber, a device for identifying and/or synthesizing chemicals or biological materials, such as a spectrometer, a fluorometer, a protein or nucleic acid sequencer or a synthesizer. Alternatively, source 402 may include an integrated system for processing samples containing nucleic acids and/or for amplifying nucleic acids. This system may include apparatus for processes such as polymerase chain reaction (PCR), nucleic acid sequence-based amplification (NASBA), ligase chain reaction (LCR), strand displacement amplification (SDA), transcription mediated amplification (TMA), amplification through generation of branched chains, and the like. Source 402 may comprise the flow PCR amplification devices described in U.S. Pat. Nos. 5,716,842 and 5,270,183, hereby incorporated by reference.

Reagent source 404 comprises a conventional device for providing one or more reagents, such as ECL coreactant, binding reagents, ECL label, a suspension of magnetic beads, and the like. For example, source 404 may include one or more pumps, valves, tubing, containers for reagents, reagent identification devices (e.g. bar codes or magnetic strips), meters, flow control devices and reagent preparation devices, or a combination thereof.

Fluid distribution network 406 routes sample(s) from sample source 402 and reagent(s) from reagent source 404 to one or more of ECL modules 408A–D. Network 406 may comprise one or more sample probes, pipettes, pumps, valves, tubing, meters, flow control devices, sample preparation devices, and processing devices, or a combination thereof. Such processing devices may include filters, mixing chambers, reaction chambers and the like. Preferably, network 406 is controlled by controller 412 and powered by power supply 414. Alternatively, network 406 is manually controlled.

In an alternate embodiment, sample source 402 and/or reagent source 404 comprise individual removable cartridges containing sample and/or reagent. Correspondingly, fluid distribution network 406 comprises a cartridge receptacle for receiving a sample source 402 cartridge and/or a reagent source 404 cartridge. The individual removable cartridges may include processing devices such as filters, mixing chambers, reaction chambers and the like.

One embodiment of system 400 of the invention is a device for conducting assays in multi-well (e.g. 96-well and 384-well) plates. Sample source 402 is a multi-well plate (e.g. a standard format 96 well or 384 well plate) that may include identification (e.g. bar codes or magnetic strips). Reagent source 404 is one or more containers that may include identification (e.g. bar codes or magnetic strips). Fluid distribution network 406 includes fluid connections to source 404, 1–12 fluid probes for sampling fluid from multi-well plates, valves, pumps, and tubing, and devices for controlling the temperature of fluids (e.g. heaters). This embodiment includes between 1 and 12 ECL measuring modules 408 as described in FIG. 5 (see descriptions of modules 408A–D below). Waste 410 is a conventional device for handling waste and may comprise a fluid line to a drain, a waste bottle, or an absorbent pad. Waste 410 may include reagents for neutralizing chemicals, for sterilizing biomaterials, or for neutralizing, inactivating, or detoxifying chemicals or other reagents. Power supply 414 is a conventional power supply. Controller 412 may incorporate a central processing unit, a keypad, a display screen, status indicators, data storage devices, software for instrument control and data analysis, devices that monitor the presence and placement of the multi-well plates, devices for identifying reagents, samples and multi-well plates (e.g. bar code readers, magnetic strip readers, modems), printing devices, network interface hardware and software (e.g. a network card or modem), keyboards and a mouse.

In operation, controller 412 identifies samples and reagents through use of identification devices and ensures that multi-well-plates 402 are correctly positioned. Controller 412 instructs fluid distribution network 406 to use fluid probes to obtain samples from multi-well plates 402 and to distribute the samples to ECL measurement modules 408. Controller 412 also instructs fluid distribution network 406 to distribute reagents from reagent source 404 and to deliver these reagents to ECL measurement modules 408. In a preferred embodiment, eight fluid probes are used to sample one column of wells in a 96-well plate; these samples are then distributed through fluid distribution network 406 to eight ECL measurement modules 408. Controller 412 instructs ECL modules 408 to conduct ECL measurements; controller 412 receives data from ECL modules 408, processes and analyses the data, and when appropriate, displays and stores the data.

ECL modules 408A, 408B, 408C, and 408D are independent ECL modules. A preferred embodiment of such an ECL module has been described above in connection with FIG. 5. Specifically, ECL modules 408A–D should each include main interface 210, main controller 214, heater 216, amplifier 218, flow cell 120, magnet detector 220, magnet controller 222, and temperature controller 224. In an alternate embodiment, ECL modules 408A–D include only main interface 210, main controller 214, flow cell 120, magnet detector 220, magnet controller 222, and temperature controller 224. Optionally, magnet detector 220 and/or magnet controller 222 may be omitted. In another alternate embodiment, ECL modules 408A–D include only main interface 210, main controller 214 and flow cell 120.

Although ECL modules 408A–D are shown coupled to controller 412 and power supply 414 in parallel, such parallel connections may be replaced by a serial connection among ECL modules 408A–D, controller 412, and power supply 414.

Waste repository 410 is a conventional waste receiving device or system and may include a combination of pumps, valves, tubing, containers for waste, meters and flow control devices.

Controller 412 is a control device for controlling the operation of fluid distribution network 406 and ECL modules 408A–D. Controller 412 may comprise a microcontroller or a microprocessor-based control system. Alternatively, controller 412 may include a device for storing ECL data and may utilize data analysis software to analyze and display data from ongoing ECL measurements. Optionally, controller 412 comprises a storage device, such as a semiconductor memory, magnetic storage media, optical storage media, magneto-optical storage media, and the like. Controller 412 may include devices for identification of samples and reagents (e.g. bar code readers or magnetic strip readers). Additionally, controller 412 may be integrated with a network or central computing system that stores data, reconciles records or performs accounting or billing functions or yet other functions. Optionally, controller 412 is adapted for remote communication with other computer systems. It is preferred that controller 412 communicate with other components of system 400 through standard data transmission protocols such as RS-232 or I²C. Controller 412 may utilize serial or parallel communication protocols in communicating with ECL modules 408A–D.

Controller 412 may be integrated with other instruments used in the medical environment, e.g. patient monitoring systems that include ECG, respiration monitors, temperature monitors, blood pressure monitors, blood chemistry analyzers, oxygen monitors and the like. Controller 412 may be integrated with other devices in the same physical housing or may be integrated through a networked connection.

In a further embodiment, controller 412 includes a user interface through which a user may control the operation of system 400. Such interface may include an input device, such as a keypad or a touch screen as well as an output device, such as a display or a printer. Through the user interface, controller 412 may display ECL measurement data, analysis of such data, and information regarding the performance and operational characteristics of system 400.

Power supply 414 is a conventional power supply unit. Although shown directly connected to each of fluid distribution network 406 and ECL modules 408A–D, such connections may be omitted if power supply 414 is coupled to controller 412 which may itself route power to each of fluid distribution network 406, and ECL modules 408A–D.

It is desired that ECL signals reported by different ECL modules 408A–D to controller 412 be directly comparable to one another. Since slight variations in the operational characteristics of each ECL module may affect the ability of the particular module to induce and detect electrochemiluminescence, the invention provides apparatus and methodology for calibrating and/or normalizing the operation of multiple ECL modules. According to this procedure, each ECL module is tested with a set of reference samples to generate respective sets of measured values. One of the ECL modules may be designated the reference module and its measured values designated as reference values. Alternatively, a reference ECL module may be tested with the set of reference samples to produce reference values. From the measured values and the reference values, controller 412 or an external calibration/normalization device calculates for each ECL module a correction transform function such that when the correction transform function is applied to the measured values, values approaching the reference values are produced. In the simplest case, each ECL module is normalized so that when supplied with a certain reference sample the module will output the same reference signal ($S_R$).

Preferably, the correction transform function is generated within an ECL module, or provided thereto by controller 412 or by an external device. Such correction transform function may be implemented within an ECL module by adjusting the amplification gain applied to the light detector signal ($S_D$), so that the amplified light detector signal ($S_{AR}$) produced when the reference sample is tested equals $S_R$. Alternatively, correction may be carried out by calculating a correction transform function $F_C = f(S_R, S_{AR})$ and applying the correction transform function to further amplified light detector signals ($S_A$) such that the output signal ($S_O$) of the ECL module is $S_O = F_C(S_A)$. Preferably, $F_C$ or the parameters of the correction transform function is stored in a memory within the particular ECL module and correction is implemented by the microcontroller internal to that module. Following calibration/normalization, the ECL modules should be completely interchangeable and comparable. In an alternate method, correction is achieved by a computer or microcontroller external to the ECL module, such as controller 412. Controller 412 may store in its memory an $F_C$ for each ECL module it controls.

Through individual main interfaces 210, each of ECL modules 408A–D are coupled to other components of system 400. Accordingly, individual ECL modules are conveniently removed and replaced.

Optionally, ECL modules 408A–D share a common light detection device provided in controller 412 and are optically coupled thereto via an optical connector such as a fiber optic line.

In operation, fluid distribution network 406, under the control of controller 412, retrieves one or more samples from sample source 402 and, optionally, one or more reagents from reagent source 404. Power supply supplies necessary power to network 406, ECL modules 408A–D, and controller 412. The sample(s) and reagent(s) are distributed to one or more of ECL modules 408A–D. Controller 412 controls each of ECL modules 408A–D to conduct at least one ECL assay upon the sample(s), utilizing selected reagent(s). Results from the ECL assays are provided to controller 412. Controller 412 controls fluid distribution network 406 to draw additional sample(s) and/or reagent(s) from sources 402 and 404, respectively, and provide same to particular ECL modules as the ECL assays are completed. The additional fluid displaces the assayed materials which are flushed to waste repository 410.

FIGS. 8A and 8B illustrate external views of certain components of system 400. In FIG. 8A, an ECL module 408A is shown comprising an enclosure 448A, a pair of rails 450A, fluid connectors 452A and 456A, and electrical connector 454A. It is preferred that all of ECL modules 408A–D have the same external features and elements as shown in FIG. 8A. For point of reference, it should be understood that fluid connectors 452A and 456A together with electrical connector 454A comprise a main interface 210, as discussed above.

Enclosure 448A is a rigid enclosure for containing the components of ECL module 408A and is preferably light-tight, thermally-insulated, and electrically conductive to shield the components of the ECL module from external environmental variations. ECL module 408A has a volume less than 50 cubic inches; preferably it has volume less than 25 cubic inches. A pair of rails 450A are attached to enclosure 448A for mechanical engagement with complementary structures in chassis 458 of system 400 (shown in FIG. 8B). Rails 450A may be integral to enclosure 448A. Alternatively, rails 450A could be replaced with another mechanical engagement device for securely connecting ECL module 408A and chassis 458.

Fluid connectors 452A and 456A provide connections for fluid input to and output from ECL module 408A. For example, fluid connector 452A may connect to heater 216, or directly to flow cell 120, of module 408A. Similarly, fluid connector 456A may connect to the fluid output of flow cell 120. Electrical connector 454A provides a connection for power, data, and control signals. Preferably, electrical connector 454A includes a printed circuit board connector. Power connections in connector 454A may connect directly to main controller 214 and temperature controller 224 of module 408A. Data and control signal connections in connector 454A may connect directly to main controller 214.

In FIG. 8B, a chassis 458 of system 400 is illustrated. Chassis 458, a rigid enclosure for containing the components of system 400, includes a number of module receptacles 460A–D. Optionally, chassis 458 may be insulated and include a heater or a conventional temperature controller. Nodule receptacle 460A includes grooves 462A, fluid connectors 464A and 468B, and electrical connector 466A. As shown, module receptacles 460A–D have the same features and include the same elements.

Grooves 462A are adapted for complementary engagement with rails 450A of enclosure 448A. Grooves 462A may comprise separate structures attached to chassis 458A. Preferably, rails 450A and grooves 462A provide a facile, secure, yet removable structural connection between ECL module 408A and chassis 458. Rails 450 and grooves 462A should be arranged to minimize the potential for damage to connectors 452A, 454A, and 456A of module 408A during insertion of module 408A into chassis 458 and to prevent misaligned insertion. Removable coupling of the ECL modules to chassis 458 is preferred to allow for quick and easy replacement of the modules. Of course, many conventional configurations of mechanical engagement structures and mechanisms may be substituted for rails 450 and grooves 462A. Preferably, the mechanical fluid and electrical connections are engaged or disengaged together in one operation. It is an important feature of this invention that the connectors can be engaged or disengaged readily, and in some embodiments, without fully interrupting the function of the device (e.g. "hot-swapping").

Fluid connectors 464A and 468A provide connections for fluid exchange with system 400. Preferably, fluid connector 464A is connectable to fluid connector 456 and itself connects to waste repository 410. Fluid output from a flow cell 120 is thus routed to waste repository 410. Fluid connector 468A is preferably connectable to fluid connector 452A and itself connects to fluid distribution network 402. Sample(s) and/or reagent(s) are distributed by fluid distribution network 402 via connectors 468A and 452A to heater 216 or flow cell 120. Electrical connector 466A is connectable to electrical connector 454 and itself connects to controller 412 and/or power supply 414. It is preferred that the fluid and electrical connections be made simply by sliding an ECL module into one of module receptacles 460A–D. Preferably, fluid connectors 452A, 456A, 464A and 468A are self-sealing on disengagement and/or self-opening on engagement to prevent leakage of fluid or fluid path obstruction.

System 400 is adapted for integration into diagnostic devices for performing large numbers of chemical or biochemical analyses at very high speeds. A high volume of diagnostic tests can be performed by operating a plurality of ECL modules in parallel. By carrying out multiple ECL assays simultaneously, overall assay throughput can be dramatically increased. In one embodiment, more than 150 assay measurements are conducted in one hour. In a preferred embodiment, more than 500 assay measurements are conducted in one hour. In a more preferred embodiment, more than 750 assay measurements are conducted in one hour. In a still more preferred embodiment, more than 10,000 assay measurements are conducted in one hour. On a system-wide basis, coordination of the ECL modules and processing of data therefrom may be accelerated by utilizing parallel connections to the ECL modules for the transmission of control and data signals. However, in certain applications serial connections of control and data signals among ECL modules improves system performance.

Advantageously, a precise number of ECL modules may be incorporated into a system to fit the precise needs of the application. System 400 is easily modified by changing the number of ECL modules.

For some applications it is advantageous to have an assay system capable of performing ECL-based assays as well as assays employing other detection technologies, e.g., fluorescence, optical absorbance, chemiluminescence, potentiometry, amperometry, and other conventional diagnostic detection methods. See, e.g., Tietz Textbook of Clinical Chemistry. 2nd Edition, C. Burtis and E. Ashwood, Eds., W. B. Saunders Co. Philadelphia, 1994 and The Immunoassay Handbook, D. Wild, Ed., Stackton Press: New York, 1994, both hereby incorporated by reference. The modular nature of the ECL measurement module allows for the straightforward development of such hybrid systems. FIG. 9A illustrates a hybrid assay system 500 for conducting an ECL assay and/or another assay upon a single sample. System 500 comprises sample source 402, reagent source 404, a fluid distribution network 502, an ECL module 504, an assay device 506, waste repository 410, and a controller 508. A detailed description of these subsystems has already been presented above. Sample source 402 and reagent source 404 are coupled to fluid distribution network 502 and provide fluids thereto.

Fluid distribution network 502, routes sample(s) from sample source 402 and reagent(s) from reagent source 404 to ECL module 504. Network 502 may comprise one or more sample probes, pipettes, pumps, valves, tubing, meters, filters, processing devices, mixing chambers or reaction chambers and other apparatus as described above, or a combination thereof. Preferably, network 502 is controlled by controller 508, or alternatively, network 502 is manually controlled. In an alternate embodiment, sample source 402 and/or reagent source 404 comprise individual removable cartridges containing sample and/or reagent. Correspondingly, fluid distribution network 502 comprises a cartridge receptacle for receiving a sample source 402 cartridge and/or a reagent source 404 cartridge.

ECL module 504 is an independent ECL module as described above in connection with FIG. 5. ECL module 504 is controlled by controller 508 and may be controlled to pass an input fluid to its output without conducting an assay. ECL module 504 contains the several elements described above in connection with FIG. 7.

Assay device 506 is a conventional assay device, such as an assay device utilizing fluorescence, optical properties, chemiluminescence, potentiometry, amperometry or other phenomena. Assay device 506 may also include e.g., a separation device, such as a chromatography instrument or an electrophoresis instrument or an analytical device e.g. a gas chromatograph or a mass spectrometer. Assay device 506 receives fluid output from ECL module 504. Assay device 506 is controlled by controller 508 and may be controlled to pass an input fluid to its output without conducting an assay. Fluid output be assay device 506 is routed to waste receptacle 410.

Controller 508 is a control device for controlling the operation of fluid distribution network 502, ECL module 504, and assay device 506. Controller 508 may comprise a microcontroller, a microprocessor-based control system or other controller and may include a device for storing ECL data and may utilize data analysis software to analyze and display data from ongoing ECL measurements. Controller 508 may be integrated with a network or central computing system and may be adapted for remote communication with other computer systems as described above with respect to controller 412 in connection with FIG. 7.

In a further embodiment, controller 508 includes a user interface through which a user may control the operation of system 500. Such interface may include input and output devices as described above. Through the user interface, controller 508 may display ECL measurement data, analysis of such data, and information regarding the performance and operational characteristics of system 500.

In operation, fluid distribution network 502, under the control of controller 508, retrieves one or more samples from sample source 402 and, optionally, one or more reagents from reagent source 404. The sample(s) and reagent (s) are distributed to ECL module 504 as described above with respect to fluid distribution network 406 in connection with FIG. 7. Controller 508 may control ECL module 504 to conduct one or more ECL assay upon the sample(s), utilizing selected reagent(s), or to not conduct an assay at all. Results from the ECL assay are provided to controller 508. Controller 508 controls fluid distribution network 502 to draw additional sample(s) and/or reagent(s) from sources 402 and 404, respectively, and provide same to ECL module 504. The additional fluid causes the materials within the module to flow to assay device 506.

Controller 508 may control assay device 506 to conduct one or more assays upon the sample(s), utilizing selected reagent(s), or to not conduct an assay at all. Results from the assay are provided to controller 508. Additional fluid provided by network 502 may flush materials within device 506 to waste repository 410. Thus, one or both of module 504 and device 506 may be used to conduct measurements on a given sample.

In an alternate embodiment, system 500 includes multiple ECL modules 504 and/or multiple assay devices 506 connected in series and controlled by controller 508. FIG. 9B illustrates a hybrid assay system 550 for conducting an ECL assay and/or another assay upon a single sample. System 550 comprises sample source 402, reagent source 404, a fluid distribution network 552, ECL module 504, assay device 506, waste repository 410, a system controller 556, a device 558 and a controller 554. A detailed description of these subsystems appears above. Sample source 402 and reagent source 404 are coupled to fluid distribution network 552 and provide fluids thereto.

Fluid distribution network 552 includes subsystems described above. It routes sample(s) from sample source 402 and reagent(s) from reagent source 404 to ECL module 504 and to assay device 506. Network 552 is controlled by controller 554 or manually. In an alternate embodiment, sample source 402 and/or reagent source 404 comprise individual removable cartridges containing sample and/or reagent. Correspondingly, fluid distribution network 552 comprises a cartridge receptacle for receiving a sample source 402 cartridge and/or a reagent source 404 cartridge. A fluid connection between ECL module 504 and assay device 506 may optionally be omitted.

Controller 554 is a control device for controlling the operation of fluid distribution network 552, ECL module 504, and assay device 506. Operation of controller 554 may be controlled by system controller 556. Controller 554 is as described above with respect to controller 412 in connection with FIG. 7. In a further embodiment, controller 554 includes a user interface through which a user may control the operation of system 550. Such interface may include input and output devices as discussed above.

System controller 556 comprises a system control device, coupled to controller 554 and to device 558. Controller 556 is preferably a microcontroller or a microprocessor-based computer such as a personal computer, a network server or the like. Controller 556 may be integrated with a network or central computing system that stores data, reconciles records or performs accounting or billing functions or yet other functions. Optionally, controller 556 is adapted for remote communication with other computer systems. It is preferred that controller 556 utilize standard data transmission protocols such as RS-232 or $I^2C$ to communicate with other components of system 550. Controller 556 may utilize serial or parallel communication protocols. System controller 556 controls the operation of system 550 through controller 554 as well as the operation of device 558. Controller 556 may collect and process data from ECL module 504, assay device 506 and device 558. It may also include an instrument interface and control output to display devices (not shown). Optionally, system controller 556 may be omitted.

Device 558 provides additional information, data and control signals that may be additional to, incorporated into, or used to generate or process information, data and control signals provided by devices 504 and 506 and controllers 554 and 556. Device 558 comprises one or more conventional devices including patient monitoring devices, analytical equipment, instrument controlling devices, and the like. Patient monitoring devices may include cardiac monitors and performance indicators (e.g. EKG), respiration monitors, blood pressure monitors, temperature monitors, blood gas monitors (for example an oxygen electrode, blood chemistry monitors (e.g. devices that use ion selective electrodes), drug/anesthesia monitors, imaging equipment and other conventional devices. Analytical equipment includes equipment for chemical and biochemical analysis. Instrument controlling devices include remote controls, data input devices, data output devices, and communication devices. Optionally, device 558 may be omitted.

In operation, fluid distribution network 552, under the control of controller 554, retrieves one or more samples from sample source 402 and, optionally, one or more reagents from reagent source 404. Controller 554 may be controlled by system controller 556 to commence such operation. The sample(s) and reagent(s) are distributed to either or both of ECL module 504 and assay device 506. Controller 554 may control ECL module 504 to conduct one or more ECL assays upon the sample(s), utilizing selected reagent(s), or to not conduct an assay at all. Controller 554 may control assay device 506 to conduct one or more assays upon the sample(s), utilizing selected reagent(s), or to not conduct an assay at all. Results from the ECL assay and the other assay are provided to controller 554 and, optionally, to system controller 556.

System controller 556 provides overall system coordination by controlling the operation of controller 554 and device 558. Data and other signals from devices 504, 506 and 558 and controller 554 are received by controller 556. Controller 556 processes, stores and/or displays these data and signals. Such processing may include data reduction and analysis and organization of the data using expert system algorithms to produce other information. Controller 556 may also send data and signals to devices 504, 506 and 558 and to controller 554. Controller 556 may also send data and signals to output devices (e.g. printers, monitors, etc.) (not shown).

Controller 554 controls fluid distribution network 552 to draw additional sample(s) and/or reagent(s) from sources 402 and 404, respectively, and provide same to either or both of ECL module 504 and assay device 506. The additional fluid causes the materials within module 504 and/or assay device 506 to flow to waste repository 410. Thus, one or both of module 504 and device 506 may be used to conduct measurements on a given sample. In an alternate embodiment, system 550 includes multiple ECL modules 504 and/or multiple assay devices 506 connected in parallel and controlled by controller 554.

In another operation, fluid distribution network 552, under the control of controller 554, retrieves one or more samples from sample source 402 and, optionally, one or more reagents from reagent source 404. Controller 554 may be controlled by system controller 556 to commence such operation. The sample(s) and reagent(s) are distributed to ECL module 504. Controller 554 controls ECL module 504 to conduct one or more ECL assays upon the sample(s), utilizing selected reagent(s), or to not conduct an assay at all. The sample(s) and reagent(s) are then distributed from ECL module 504 to assay device 506. Controller 554 controls assay device 506 to conduct one or more assays upon the sample(s), utilizing selected reagent(s), or to not conduct an assay at all. Results from the ECL assay and the other assay are provided to controller 554 and, optionally, to system controller 556. Optionally, the fluid path between fluid distribution network 552 and assay device 506 is omitted. Optionally, the fluid path between ECL module 504 and waste 410 may be omitted.

Controller 554 controls fluid distribution network 552 to draw additional sample(s) and/or reagent(s) from sources 402 and 404, respectively, and provide same to ECL module 504 and therethrough to assay device 506 (via ECL module 504). The additional fluid causes the materials within module 504 and/or assay device 506 to flow to waste repository 410. Thus, one or both of module 504 and device 506 may be used to conduct measurements on a given sample. In an alternate embodiment, system 550 includes multiple ECL modules 504 and/or multiple assay devices 506 connected in series and controlled by controller 554.

In another operation, fluid distribution network 552, under the control of controller 554, retrieves one or more samples from sample source 402 and, optionally, one or more reagents from reagent source 404. Controller 554 may be controlled by system controller 556 to commence such operation. The sample(s) and reagent(s) are distributed to assay device 506. Controller 554 controls assay device 506 to conduct one or more assays upon the sample(s), utilizing selected reagent(s), or to not conduct an assay at all. The sample(s) and reagent(s) are then distributed from assay device 506 to ECL module 504. Controller 554 controls ECL module 504 to conduct one or more ECL assays upon the sample(s), utilizing selected reagent(s), or to not conduct an assay at all. Results from the ECL assay and other assay are provided to controller 554 and, optionally, to system controller 556. Optionally, the fluid path between fluid distribution network 552 and ECL module 504 may be omitted. Optionally, the fluid path between the assay device 506 and waste 410 can be omitted.

Controller 554 controls fluid distribution network 552 to draw additional sample(s) and/or reagent(s) from sources 402 and 404, respectively, and provide same to assay device 506 and therethrough to ECL module 504. The additional fluid causes the materials within module 504 and/or assay device 506 to flow to waste repository 410. Thus, one or both of module 504 and device 506 may be used to conduct measurements on a given sample. In an alternate embodiment, system 550 includes multiple ECL modules 504 and/or multiple assay devices 506 connected in series and controlled by controller 554.

FIGS. 10A, 10B, 10C and 10D illustrate external views of certain components of system 550. FIG. 10A depicts an external view of integrated assay subsystem 560 comprising an enclosure 1448A, a pair of rails 1450A, and electrical connector 1454A. Assay system 560 is securely mounted within enclosure 1448A. Enclosure 1448A is an enclosure for the components of assay subsystem 560 and is preferably light-tight, thermally-insulated, and electrically conductive to shield the components of the subsystem from external environmental variations. A pair of rails 1450A are attached to enclosure 1448A for mechanical engagement with complementary structures in chassis 1458, e.g., grooves 462A (shown in FIG. 10D). Rails 1450A may be integral to enclosure 1448A. Alternatively, rails 1450A could be replaced with another mechanical engagement device for securely connecting enclosure 1448A to chassis 1458. Electrical connector 1454A provides a connection for power, data, and control signals to or from controller 554.

FIG. 10B depicts an external view of device 558 comprising an enclosure 1448B, a pair of rails 1450B, and electrical connector 1454B. Device 558 is securely mounted within enclosure 1448B. Enclosure 1448B is an enclosure for the components of device 558. A pair of rails 1450B are attached to enclosure 1448B for mechanical engagement with complementary structures in chassis 1458, e.g., grooves 462A (shown in FIG. 10D). Rails 1450B may be integral to enclosure 1448B. Alternatively, rails 1450B could be replaced with another mechanical engagement device for securely connecting enclosure 1448B to chassis 1458. Electrical connector 1454B provides a connection for power, data, and control signals to or from device 558.

FIG. 10C depicts an external view of system controller 556 comprising an enclosure 1448C, a pair of rails 1450C, and electrical connector 1454C. Controller 556 is securely mounted within enclosure 1448C. Enclosure 1448C is an enclosure for the components of controller 556. A pair of rails 1450C are attached to enclosure 1448C for mechanical engagement with complementary structures in chassis 1458, e.g., grooves 462A (shown in FIG. 10D). Rails 1450C may be integral to enclosure 1448C. Alternatively, rails 1450C could be replaced with another mechanical engagement device for securely connecting enclosure 1448C and chassis 1458. Electrical connector 1454C provides a connection for power, data, and control signals to or from controller 556.

In FIG. 10D, a chassis 1458 is illustrated. Chassis 1458, a rigid enclosure for containing one or more of subsystem 560, device 558 and/or system controller 556, includes a number of system receptacles 1460A–D. Optionally, chassis 1458 may be insulated and include a heater or a conventional temperature controller. System receptacles 1460A–D includes grooves 462A–D and electrical connectors 466A–D, respectively. As shown, system receptacles 1460A–D have the same features and include the same elements. Thus, it is preferred that each of enclosures 1448A–C be complementary to each of system receptacles 1460A–D.

Grooves 462A–D are adapted for complementary engagement with rails 1450A–C of enclosures 1448A–C. Grooves 462A–C may comprise separate structures attached to chassis 1458. Preferably, rails 1450A–C and grooves 462A–D provide facile, secure, yet removable structural connections between chassis 1458 and enclosures 1448A, 1448B, and 1448C.

The Rails and grooves should be arranged to minimize the potential for damage to the electrical connector of the enclosure during its insertion into the electrical connector of the chassis and to prevent misaligned insertion. Removable coupling of the enclosure(s) with chassis 1458 is preferred to allow for quick and easy replacement of the enclosed systems and devices. Of course, many conventional configurations of mechanical engagement structures and mechanisms may be substituted for the rails and grooves. Preferably, the mechanical and electrical connections are engaged or disengaged together in one operation. It is an important feature of this invention that the connectors can be engaged or disengaged readily, and in some embodiments, without fully interrupting the function of the device (e.g., "hot-swapping").

Electrical connectors 466A–D are adopted for connection to any of electrical connectors 1454A–C. Electrical connectors 466A–D may be connected to each other in series. Optionally, connectors 466A–D may also be connected to a power supply (not shown). Alternatively, the electrical connector to which system controller 556 is (or will be) connected may itself be connected to the connectors in series, parallel, or a combination thereof. It is preferred that the electrical connections be made simply by sliding an enclosure 1448A–C into one of system receptacles 1460A–D. The arrangement of mechanical and electrical connections between receptacles 1460A–D and subsystem 560, device 558 and system controller 556 are similar to those described above in connection with subsystem 560 and receptacle 1460A.

In one embodiment, the receptacles 460B–D are identical to receptacle 460A. In another embodiment, any of receptacles 460A–D can be engaged to any of system 560, device 558, and controller 556. In another embodiment, each of receptacles 460 A–D are designed specifically for one of system 560, device 558, and controller 556 and, optionally, grooves 462A–D differ to accommodate differences among rails 1450A, 1450B, and 1450C and to prevent insertion of a module into a receptacle not intended for that module. Although FIG. 10D shows four receptacles 1460A–D, chassis 1458 may be expanded or contracted to include any number of receptacles.

According to another embodiment of the invention, a single module that can conduct both ECL measurements and non-ECL measurements is provided. Such a multiple measurement ECL module is capable of making ECL measurements and one or more of the following type of measurements: optical absorbance, fluorescence, phosphorescence and light scattering. FIG. 11 illustrates an exploded view of a flow cell 600 capable of both ECL measurements and non-ECL measurements. Flow cell 600 comprises light detectors 122 and 612, optical filter 123, conductive window 124, shield 126, reference electrode 128, couplings 130 and 132, cell components 134 and 604, counter electrode 136, gaskets 138 and 614, light generator 602, working electrode 140, cell base 142, pivot arm 144, magnet 146 and magnet detector 147. Detailed descriptions of light detector 122, optical filter 123, conductive window 124, shield 126, reference electrode 128, couplings 130 and 132, cell component 134, counter electrode 136, gasket 138, light generator 602, working electrode 140, cell base 142, pivot arm 144, magnet 146 and magnet detector 147 have been provided hereinabove with reference to FIG. 3A.

Light detector 612 is a conventional light detection device, such as a CCD or photodiode array, for detecting light in ECL chamber 139. Detector 612 may have limited sensitivity to certain wavelengths of light or include optical devices, such as a filter, to allow detection of particular types of light. Preferably, detector 612 is configured to allow the measurement of individual spectral components of light. Optionally, light detector 612 is omitted.

Light generator 602 is a conventional light source for conducting assays. Generator 602 may be utilized to generate any usual light frequency for fluorescence or phosphorescence measurements, measurement of optical properties such as absorption and light scattering, and the like. Generator 602 may include a wavelength selection device, such as a diffraction grating or filter, to select light with certain spectral properties. As shown, it is preferred that light generator 602 and light detector 612 include a fiber optic extension for carrying light directly from ECL chamber 139. Gasket 614 is identical in all respects to gasket 138.

Cell component 604 comprises the same material as cell component 134. As shown, component 604 includes an opening 610 which has the cross-sectional shape as that of gasket opening 137. Opening 610 defines a portion of the sides of ECL chamber 139. Two bore holes 606 and 608 extend from opposite sides of component 604 towards but not intersecting with opening 610. Bore holes 606 and 608 are adapted to receive the fiber optic extensions of light generator 602 and light detector 612. In an alternate embodiment, bore holes 606 and 608 do intersect opening 610. Also, cell component 604 includes two gasket grooves 141, one on the top surface and one on the bottom surface (not shown) of cell component 604.

Flow cell 600 operates similarly to flow cell 120, previously described, but with the added capability of conducting optical absorbance, fluorescence, phosphorescence and light scattering measurements and like measurements of optical properties. Light generator 602 is controlled by a controller (not shown) to emit light through its optics extension to ECL chamber 139. Light detector 612 detects either the transmitted, scattered or emitted light or other light generated within ECL chamber 139. The generated light may be induced by the emitted light or be the result of ECL or both.

In an alternate embodiment, bore holes 606 and 608 are arranged at an angle to one another such that light emitted from light generator 602 does not substantially impinge upon light detector 612. With such an arrangement, light scattering measurements, luminescence measurements, and the like may be conducted. Optionally, light detector 122 is utilized for the detecting light for optical absorbance, fluorescence, phosphorescence and light scattering measurements and like measurements of optical properties.

The apparatus and methods of the invention as described above may be generally applied to conducting ECL assays and assays using other detection techniques. Assays that may be conducted include those described in the following documents, hereby incorporated by reference: U.S. Pat. No. 5,221,605; U.S. Pat. No. 5,527,710; U.S. Pat. No. 5,591,581; U.S. Pat. No. 5,597,910; U.S. Pat. No. 5,610,075; U.S. Pat. No. 5,641,623; U.S. Pat. No. 5,643,713; Published PCT Application No. WO 9628538; *Tietz Textbook of Clinical Chemistry*, 2nd Edition, C. Burtis and E. Ashwood, Eds., W. B. Saunders Co. Philadelphia, 1994 and *The Immunoassay Handbook*, D. Wild, Ed., Stackton Press: New York, 1994. For example, the foregoing apparatus and methodology may implement binding assays in competitive and noncompetitive formats, e.g., receptor-ligand binding assays, nucleic acid hybridization assays, immunoassays, and the like as well as assays of enzymes or enzyme substrates by measurement of catalytic activity, assays of gasses and electrolytes (e.g., blood gasses and electrolytes), and clinical chemistry assays.

Although illustrative embodiments of the present invention and modifications thereof have been described in detail herein, it is to be understood that this invention is not limited to these precise embodiments and modifications, and that other modifications and variations may be effected therein by one skilled in the art without departing from the scope and spirit of the invention as defined by the appended claims.

What is claimed is:

1. An apparatus for the conduct of electrochemiluminescence measurements comprising:

a cell having at least one cell wall which includes a transparent portion adjacent to an ECL chamber defined within said cell;

a working electrode abutting said ECL chamber and in optical registration with said transparent portion;

a counter electrode abutting said ECL chamber; and an electrically-shielded window adjacent to and in optical registration with said transparent portion.

2. The apparatus according to claim 1 further comprising a photodetector.

3. The apparatus according to claim 1 further comprising a photodetector in optical registration with said electrically-shielded window, said transparent portion and said working electrode.

4. The apparatus according to claim 3 wherein no air gap exists between any of said photodetector, said electrically-shielded window, and said transparent portion.

5. The apparatus according to claim 3 wherein said electrically-shielded window and said transparent portion each has a refractive index of between 1.3 and 1.6.

6. The apparatus according to claim 3 wherein more than 40% of any electrochemiluminescence generated within said ECL chamber is incident upon said photodetector.

* * * * *